United States Patent [19]

Hirai et al.

[11] Patent Number: 5,098,602
[45] Date of Patent: Mar. 24, 1992

[54] NOVEL HALOGEN-CONTAINING ESTER COMPOUNDS, AND THEIR INTERMEDIATES, AND METHOD OF PRODUCING THE SAME AS WELL AS LIQUID CRYSTAL COMPOSITIONS CONTAINING THE SAME AND LIGHT SWITCHING ELEMENTS

[75] Inventors: Toshihiro Hirai; Atsushi Yoshizawa; Isa Nishiyama; Mitsuo Fukumasa; Nobuyuki Shiratori; Akihisa Yokoyama, all of Saitama, Japan

[73] Assignee: Nippon Mining Co., Ltd., Japan

[21] Appl. No.: 346,454

[22] Filed: May 2, 1989

[30] Foreign Application Priority Data

| May 11, 1988 | [JP] | Japan | 63-112334 |
| Oct. 3, 1988 | [JP] | Japan | 63-247496 |
| Mar. 2, 1989 | [JP] | Japan | 1-48452 |
| Mar. 9, 1989 | [JP] | Japan | 1-57129 |

[51] Int. Cl.$^5$ .................. C09K 19/12; C09K 19/20; C07C 69/76; C07C 69/88
[52] U.S. Cl. .................. 252/299.65; 252/299.67; 560/55; 560/59; 560/61; 560/62; 560/65; 560/73; 560/102; 560/106; 560/107; 560/108; 560/109; 560/111
[58] Field of Search .................. 252/299.65, 299.64, 252/299.67; 560/55, 59, 61, 62, 64, 65, 73, 102, 106, 107, 108, 109, 111

[56] References Cited

U.S. PATENT DOCUMENTS 4,780,242 10/1988 Miyazawa et al. ............... 252/299.65

FOREIGN PATENT DOCUMENTS

| 197677 | 10/1986 | European Pat. Off. |
| 315193 | 5/1989 | European Pat. Off. |
| 60-32748 | 2/1985 | Japan. |
| 61-43 | 1/1986 | Japan. |
| 61-22051 | 1/1986 | Japan. |
| 61-165350 | 7/1986 | Japan. |
| 61-210056 | 9/1986 | Japan. |
| 8807518 | 10/1988 | World Int. Prop. O. |

Primary Examiner—Robert L. Stoll
Assistant Examiner—Philip Tucker
Attorney, Agent, or Firm—Parkhurst, Wendel & Rossi

[57] ABSTRACT

This invention provides a novel halogen-containing ester compound represented by the following general formula (I):

$$R-A-\underset{}{\bigcirc}-(\bigcirc)_{\overline{m}}COO-(\bigcirc)_{\overline{n}}\underset{Y}{\bigcirc}-\underset{\underset{O}{\|}}{C}-\underset{\underset{C_kH_{2k+1}}{|}}{CH}-C_lH_{2l+1} \quad (I)$$

with X above the first ring after $(\bigcirc)_{\overline{m}}$ and Y above the ring before the carbonyl.

(wherein R is an alkyl group, A is selected from a single bond, —O—, —COO— and —CO—, both of X and Y are halogen atoms or either one of X and Y is a halogen atom and the other is a hydrogen atom, each of m and n is 0 or 1, m+n=0 or 1, each of k and l is an integer of 1 or more, provide k<l), a liquid crystal composition and a light switching element each containing the above compound as well as a novel fluorophenol compound represented by the following general formula (II):

$$HO-\underset{}{\bigcirc}\overset{F}{-}\underset{\underset{O}{\|}}{C}-\underset{\underset{C_kH_{2k+1}}{|}}{CH}-C_lH_{2l+1} \quad (II)$$

(wherein each of k and l is an integer of 1 or more, provided k<l) as an intermediate for the synthesis of the above ester compound and a method of producing the same.

5 Claims, 6 Drawing Sheets

FIG._1

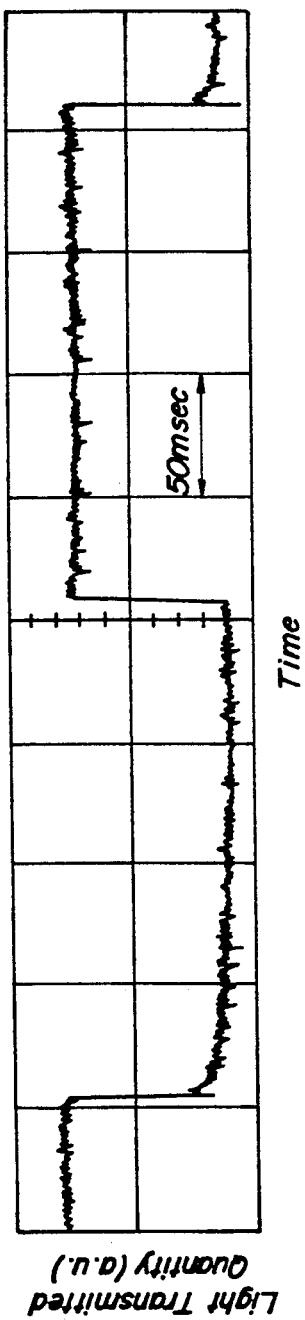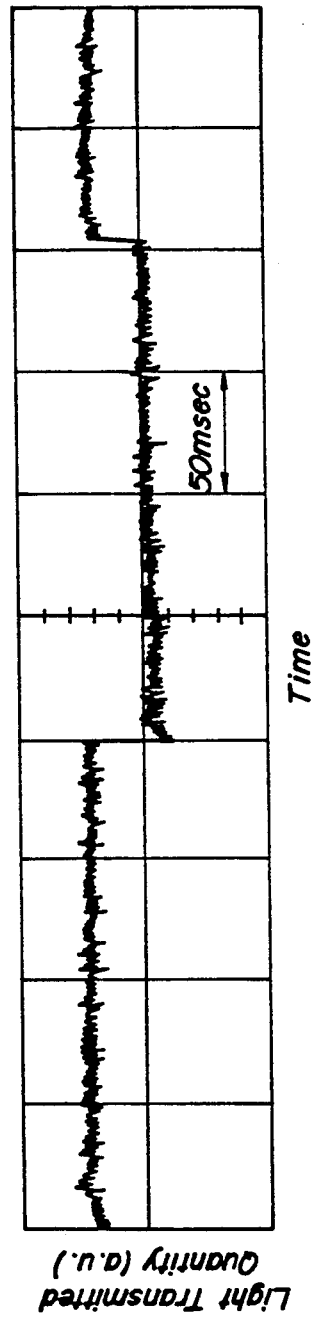

NOVEL HALOGEN-CONTAINING ESTER COMPOUNDS, AND THEIR INTERMEDIATES, AND METHOD OF PRODUCING THE SAME AS WELL AS LIQUID CRYSTAL COMPOSITIONS CONTAINING THE SAME AND LIGHT SWITCHING ELEMENTS

BACKGROUND OF THE INVENTION

1. Field of the Invention

This invention relates to novel halogen-containing ester compounds which can take a stable thermotropic liquid crystal state and can be utilized as a liquid crystalline material useful for use in optoelectronics related elements using a liquid crystal and electrochemichromism such as display for liquid crystal television receiver, optical printer head, opto-Fourier transform element, light valve and the like, their intermediates and method of producing the same as well as liquid crystal compositions containing the above compounds and light switching elements using the same.

2. Related Art Statement

Liquid crystalline compounds having asymmetric carbon in their molecule can take a chiralsmectic phase in the crystal structure and may exhibit properties as a ferroelectric liquid crystal having a fast response time, so that they are recently expected as a liquid crystalline material for displaying means requiring a high speed responsibility. As such a liquid crystalline compound, there have been proposed optically active halocarboxylic acid derivatives (Japanese Patent laid open No. 61-165350), ether compounds containing optical active group and halogen-containing phenylbiphenyl ester group (Japanese Patent laid open No. 61-210056), ester compounds containing optical active group and phenyl-biphenyl ester group (Japanese Patent laid open No. 60-32748) and so on.

As properties required in the ferroelectric liquid crystalline material, there are various requirements that the chiralsmectic C phase is exhibited over a wide temperature range inclusive of room temperature, the spontaneous polarization is large, the material is chemically stable and the like. Since these requirements are very difficult to be satisfied only by the single compound, the requirements as a liquid crystalline composition are usually satisfied by mixing some compounds.

On the other hand, the light switching element is an element for switching on and off light in accordance with external force such as electric field, magnetic field or the like. At the present, twisted nematic (TN) type system consisting of nematic liquid crystal is exclusively used as this type of the light switching element in the field for displaying elements. However, the switching element using the nematic liquid crystal has a drawback that the response is slow. Therefore, the elements using the ferroelectric liquid crystal are proposed as a light switching element having a fast responsibility instead of the nematic liquid crystal.

The halocarboxylic acid derivatives are relatively large in the spontaneous polarization, but are lacking in the light stability because they have generally carbon-halogen bond and also the temperature range showing the ferroelectricity is narrow. Furthermore, the ether compounds containing the optical active group are lacking in the light stability because of the presence of halogen, relatively large in the spontaneous polarization but narrow in the temperature range showing the ferroelectricity. Moreover, the ester compounds containing the optical active group are relatively wide in the temperature range showing the ferroelectricity, but are small in the spontaneous polarization.

That is, the liquid crystalline materials used for displaying means requiring high speed responsibility are required to have properties that the spontaneous polarization is large, the viscosity is low, the chiralsmectic C phase is exhibited over a wide temperature range inclusive of room temperature and the like. However, materials sufficiently satisfying these properties are not yet provided at the present.

Further, it is attempted to stabilize the chiralsmectic C phase by introducing halogen into a nucleus portion of the liquid crystal, or to prevent the appearance of higher smectic phase at a low temperature side of chiralsmectic phase (Saito et al, 13th Panel Discussion of Liquid Crystal 1Z06; Shoji et al, 13th Panel Discussion of Liquid Crystal 1Z13). In this case, however, the displaying elements having a sufficient high speed responsibility can not be manufactured even by using such liquid crystalline materials.

On the contrary, the inventors have previously found that compounds having an asymmetric carbon at α-position and ketone group directly bonded to benzene ring in molecule are stable against light or the like and wide in the temperature range enantiotropically forming a liquid crystalline state, and particularly when optical activity is given to the asymmetric carbon, they are rendered into a ferroelectric liquid crystal exhibiting chiralsmectic C phase and having a large spontaneous polarization and a fast response rate (International Publication No. WO88/07518).

SUMMARY OF THE INVENTION

The inventors have made further studies in order to more enhance the liquid crystal properties of the above proposed compounds, and found that some compounds among them can disappear higher smectic phase at a low temperature side of chiralsmectic C pase or approach the temperature region of chiralsmectic C phase to room temperature by introducing halogen into nucleus portion without damaging the large spontaneous polarization inherent to the ferroelectric liquid crystal or with developing larger spontaneous polarization.

The invention is based on the above knowledge and is to provide novel halogen-containing ester compounds useful as a liquid crystal composition, their intermediates and a method of producing the same as well as liquid crystal compositions containing these compounds.

It is another object of the invention to provide a liquid crystal displaying element having a high speed responsibility by using the above novel compound or the liquid crystal composition containing the same.

That is, the invention provides a novel halogen-containing ester compound represented by the following general formula (I):

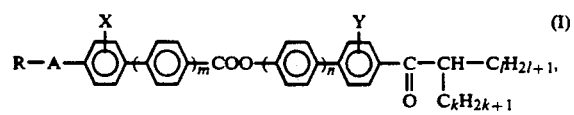

wherein R is an alkyl group, A is selected from a single bond, —O—, —COO— and —CO—, both of X and Y are halogen atoms or either of X and Y is a halogen atom and the other is a hydrogen atom, each of m and n is 0 or 1 provided m+n=0 or 1, and each of k and l is an integer of 1 or more provide k<l, a liquid crystal composition and a light switching element each containing this compound as well as a novel fluorophenol compound having the following general formula (II):

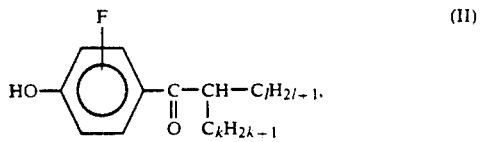

wherein k and l are the same meaning as mentioned above, as an intermediate of the above ester compound and a method of producing the same.

BRIEF DESCRIPTION OF THE DRAWINGS

The invention will be described with reference to the accompanying drawings, wherein:

FIG. 7 is a graph showing a relation between time and light transmitted quantity in the light switching element of Example 36; and FIG. 8 is a graph showing a relation between time and light transmitted quantity in the light switching element of Example 37.

DESCRIPTION OF THE PREFERRED EMBODIMENTS

Figure 1:
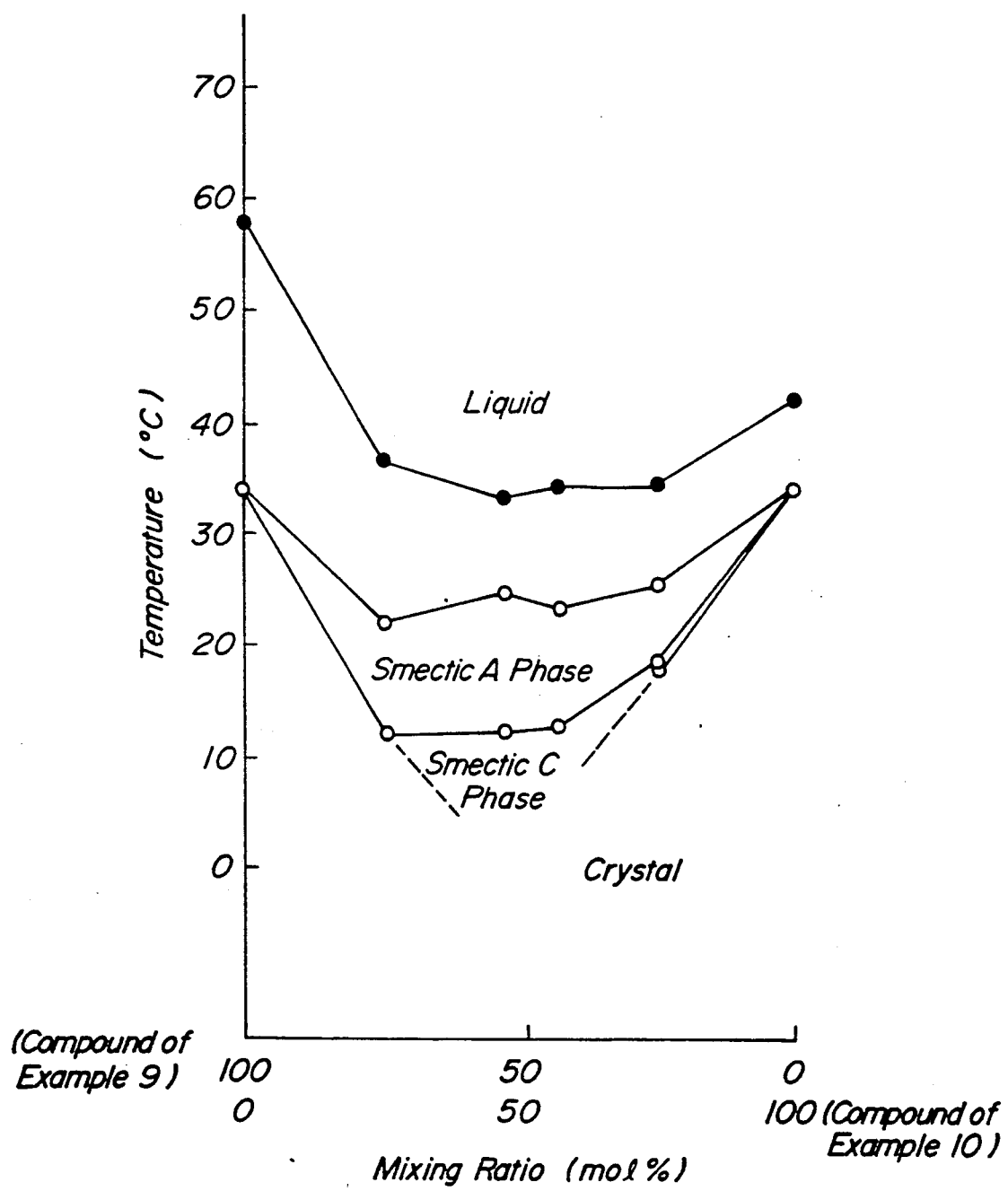
FIG. 1 is a phase diagram when 4-(2-methyloctanoyl) phenyl-3-fluoro-4 pentyloxy benzoic acid ester obtained in Example 9 and 4-(2-methyloctanoyl) phenyl-3-fluoro-4-dodecyl benzoic acid ester obtained in Example 10 are mixed at various mixing ratios.

In the above general formula (I), the alkyl group shown by R and the integer of k and l are not particularly critical, but it is preferable that R has a carbon number of up to 18 and k and l are up to 16 from a viewpoint of actual production factors such as easy availability of starting materials and the like.

Moreover, when carbon bonding $C_kH_{2k+1}$ in the above formula is an asymmetric carbon and an optical activity is introduced into the compound taking this carbon as an asymmetric center, the resulting liquid crystal exhibits a chiralsmectic C phase and is preferable as a ferroelectric liquid crystal having a very large spontaneous polarization and a fast response rate.

On the other hand, k and l are preferable to be 1-16 in the alkyl group shown by $-C_kH_{2k+1}$ or $-C_lH_{2l+1}$ in the novel fluorophenol compound of the general formula (II) as an intermediate of the formula (I) from the same reasons as mentioned above. Among such intermediates, when the carbon bonding $-C_kH_{2k+1}$ is an asymmetric carbon and the optical activity is introduced into this compound, the ferroelectric liquid crystals having a very large spontaneous polarization and a fast response rate can be synthesized in the same manner as mentioned above.

Now, the fluorophenol compounds have hitherto been said to be useful as an intermediate material for medicines, agricultural chemicals and various functionable organic materials because they have a hydroxy group having a rich reactivity. Recently, compounds having an optical activity among fluorine-containing alkoxy phenols and fluorine-containing alkoxycarbonyl phenols are watched and used as an intermediate for ferroelectric smectic liquid crystal compound using an active hydroxyl group. However, when the conventionally used fluoroalkoxy phenols and fluoroalkoxycarbonyl phenols are used as an intermediate for ferroelectric liquid crystal, there are various drawbacks that the applicable temperature becomes improper, the spontaneous polarization is small, the high speed response is poor, the uniformity is poor and the like. According to the invention, the intermediates represented by the above general formula (II) have been found as a result of various examinations for solving the aforementioned problems of the conventional fluorophenol compounds.

Examples of the novel fluorophenol compounds shown by the formula (II) and their physical and chemical properties are as follows:

2-fluoro-4-(2-methyloctanoyl) phenol

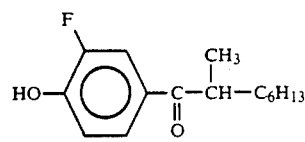

① $^1$H-NMR (in CDCl$_3$, TMS standard, ppm): 7.77(1H, t), 7.61(1H, s), 6.96(1H, t), 3.38(1H, m), 1.8–1.1(13H), 0.85(3H, t)
② IR(KBr, cm$^{-1}$) 3250, 1650, 1600
③ Mass: 252(M+)
④ $[\alpha]^{25}_D$: +27.9°

3-fluoro 4-(2-methyloctanoyl) phenol

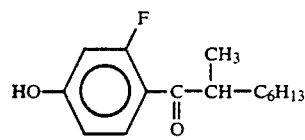

① $^1$H-NMR (in CDCl$_3$, TMS standard, ppm): 7.77(1H, t), 7.43(1H, s), 6.58(2H, m), 3.33(1H, m), 1.9–1.0(13H), 0.86(3H, t)
② IR(KBr, cm$^{-1}$): 3250, 1650, 1600
③ Mass: 252(M+)

(+)-3-fluoro-4-(2-methylnonanoyl) phenol

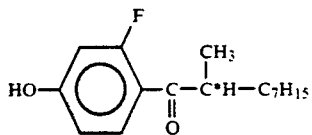

① ¹H-NMR (in CDCl₃, TMS standard, ppm): 7.8(1H, t), 7.4(1H, s), 6.6(2H, m), 3.3(1H, m), 2.0–1.0(15H), 0.9(3H, t)
② IR(KBr, cm⁻¹): 3250, 1650, 1600
③ Mass: 266(M+)

Moreover, the length of the alkyl chain of the compound shown by the formula (H) can properly be selected in accordance with the finally synthesized liquid crystal compound because it affects the temperature region and the like forming a liquid crystal state in the compound synthesized from this intermediate.

Examples of the compounds shown by the general formula (I) and their physical and chemical properties are as follows:

2-fluoro-4-(2-methyloctanoyl)phenyl-4'-octyloxybiphenyl-4-carboxylic acid ester

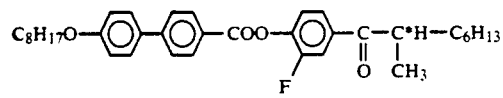

① ¹H-NMR (in CDCl₃, TMS standard, ppm): 8.25(2H, d), 7.80(2H, d), 7.70(2H, d), 7.58(2H, d), 7.40(1H, t), 7.00(2H, d), 4.0(2H, t), 3.4(1H, m), 1.85(2H, m), 1.4(20H, bs), 1.2(3H, d), 0.9(6H, t)
② IR(KBr, cm⁻¹) 2920, 2850, 1740, 1675, 1600, 1505, 1425, 1360, 1195, 1120, 1060, 825, 780

4-(2-methyloctanoyl) phenyl 3-chloro-4-octyloxy benzoic acid ester

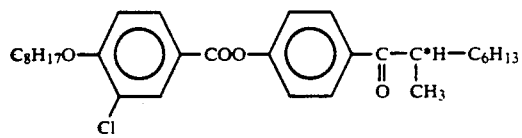

① ¹H-NMR (in CDCl₃, TMS standard, δ ppm): 8.20–6.95(7H), 4.13(t, 2H), 3.42(m, 1H), 0.89–2.0(m, 31H)
② IR(KBr, cm⁻¹): 2800, 2700, 1735, 1680, 1590
③ Mass: 500(M+)

4'-(2-methyloctanoyl) biphenyl-3-chloro-4-octyloxy benzoic acid ester

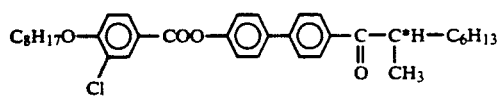

① ¹H-NMR (in CDCl₃, TMS standard, δ ppm): 8.28(d, 1H), 8.07(m, 3H), 7.70(d, 4H), 7.35(d, 2H), 7.00(d, 1H), 4.16(t, 2H), 3.50(m, 1H), 1.7–2.0(m, 4H), 1.3–1.6(m, 18H), 1.24(d, 3H), 0.80–0.95(m, 6H)
② IR(KBr, cm⁻¹): 2910, 2840, 1720, 1680, 1600, 1285, 760

4'-(2-methyloctanoyl) biphenyl-3-chloro-4-octylcarbonyloxy benzoic acid ester

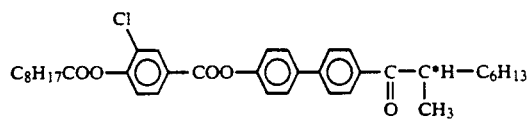

① ¹H-NMR (in CDCl₃, TMS standard, δ ppm): 7.20–8.40(m, 11H), 3.50(m, 1H), 2.62(t, 2H), 0.80–1.90(m, 31H)
② IR(KHr, cm⁻¹): 2920, 2850, 1770, 1730, 1680, 1600

2-fluoro-4-(2-methyloctanoyl) phenyl-4-nonanoyl benzoic acid ester

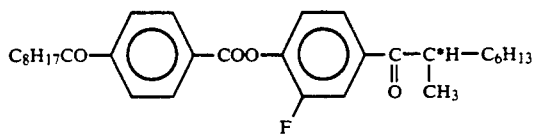

① ¹H-NMR (in CDCl₃, TMS standard, ppm): 8.34–7.30(7H), 3.36(1H, m), 3.01(2H, t), 1.8–1.1(25H), 0.88(6H, t)
② IR(KBr, cm⁻¹): 2920, 2850, 1755, 1680, 1260, 1060

2-fluoro-4-(2-methyloctanoyl) phenyl-4-decanoyloxy benzoic acid ester

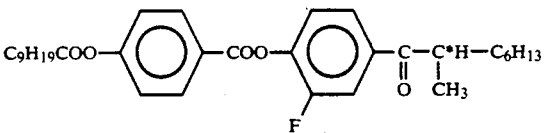

① ¹H-NMR (in CDCl₃, TMS standard, ppm): 8.28–7.20(7H), 3.37(1H, m), 2.59(2H, t), 1.8–1.1(27H), 0.88(6H, t)
② IR(KBr, cm⁻¹): 2920, 2850, 1755, 1675, 1600, 1510, 1420, 1255, 1160, 1140, 1120, 1060

2-fluoro-4 (2-methyloctanoyl) phenyl-4-octyloxy benzoic acid ester

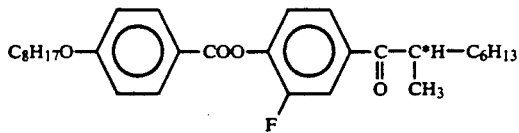

① ¹H-NMR (in CDCl₃, TMS standard, ppm): 8.16(2H, d), 7.8(2H, d), 7.4(1H, t), 7.0(2H, d), 4.05(2H, t), 3.47(1H, m), 2.0–1.0(25H), 0.90(6H, t)
② IR(KBr, cm⁻¹): 2920, 2850, 1740, 1680, 1600, 1510, 1420, 1250, 1160, 1050, 840, 760

4-(2-methyloctanoyl) phenyl-3-fluoro-4-octyloxy benzoic acid ester

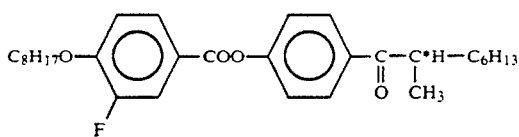

① ¹H-NMR (in CDCl₃, TMS standard, ppm): 8.09–6.94(7H, m), 4.13(2H, t), 3.42(1H, m), 2.0–1.1(25H), 1.1–0.8(6H)
② IR(KBr, cm⁻¹): 2920, 1735, 1680, 1280, 1210, 750
③ Mass: 484(M+)

4-(2-methyloctanoyl) phenyl-3-fluoro-4-pentyloxy benzoic acid ester

① ¹H-NMR (in CDCl₃, TMS standard, ppm): 8.08(4H, m), 7.33(2H, d), 7.03(1H, t), 4.13(2H, d), 3.42(1H, m), 2.0–1.1(19H), 1.1–0.8(6H)
② IR(KBr, cm⁻¹): 2920, 1725, 1675, 1615, 1300, 1210.
③ Mass: 442(M+)

4-(2-methyloctanoyl) phenyl-3-fluoro-4-dodecyloxy benzoic acid ester

① ¹H-NMR (in CDCl₃, TMS standard, ppm): 8.19–7.81(4H, m), 7.35(2H, d), 7.03(1H, t), 4.13(2H, t), 3.47(1H, m), 2.0–1.1(33H), 0.88(6H)
② IR(KBr, cm⁻¹): 2920, 1725, 1680, 1615, 1300, 1235, 750
③ Mass: 540(M+)

4-(2-methyloctanoyl) phenyl-4-fluoro 4-nonyloxy benzoic acid ester

① ¹H-NMR (in CDCl₃, TMS standard, ppm): 8.04(d, 2H), 8.0–7.85(m, 2H), 7.3(d, 2H), 7.05(t, 1H), 4.15(t, 2H), 3.47(m, 1H), 2.0–1.0(27H), 0.9(t, 6H)
② IR(KBr, cm⁻¹): 2910, 1730, 1675, 1615, 1295, 1215, 750
③ Mass: 498(M+)

4'-(2-methyloctanoyl) biphenyl-3-fluoro-4-octyloxy benzoic acid ester

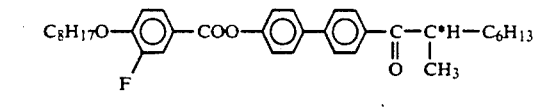

① ¹H-NMR (in CDCl₃, TMS standard, ppm): 8.20–6.95(m, 11H), 4.14(t, 2H), 3.47(m, 1H), 1.95–1.20(m, 25H), 1.00–0.80(m, 6H)
② IR(KBr, cm⁻¹) 2950, 2900, 2850, 1720, 1680, 1600, 1500

3-fluoro-4-(2-methyloctanoyl) phenyl-4'-nonylbiphenyl-4-carboxylic acid ester

① ¹H-NMR (in CDCl₃, TMS standard, ppm): 8.25(d, 2H),

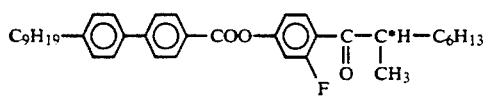

7.9(t, 1H), 7.7(d, 2H), 7.58(d, 2H), 7.33(d, 2H), 7.15(t, 2H), 3.35(m, 1H), 2.67(t, 2H), 2.0–1.0(27H).
② IR(KBr, cm⁻¹): 2920, 1735, 1680, 1605, 1270, 1230
③ Mass: 558(M+)

3-fluoro-4-(2-methyloctanoyl) phenyl-4-heptyloxy benzoic acid ester

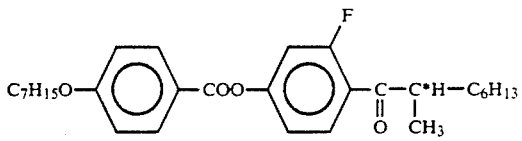

① ¹H-NMR (in CDCl₃, TMS standard, ppm): 8.1(2H, d), 7.3–6.9(4H), 4.1(2H, t), 3.3(1H, m), 2.0–1.1(23H), 0.9(6H)
② IR(KBr, cm⁻¹): 2910, 2850, 1730, 1675, 1600, 1250, 750
③ Mass: 470(M+)

4-(2-methyloctanoyl) phenyl-3-fluoro-4-nonanoyloxy benzoic acid ester

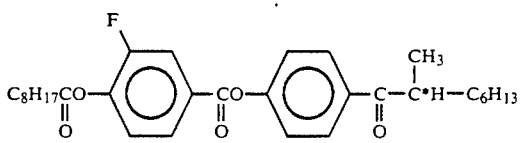

① ¹H-NMR (in CDCl₃, TMS standard, ppm): 8.15–7.85(m, 4H), 7.45–7.15(m, 3H), 3.5(m, 1H), 2.6(t, 2H), 2.0–1.0(25H), 0.9(6H)
② IR(KBr, cm⁻¹): 2910, 2850, 1780, 1740, 1680, 1300, 750
③ Mass: 512(M+)

4-(2 methylnonanoyl) phenyl-3'-fluoro-4'-octyloxybiphenyl-4-carboxylic acid ester

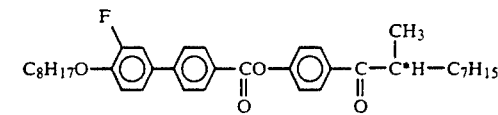

① ¹H NMR (in CDCl₃, TMS standard, ppm): 8.3(d, 2H), 8.1(d, 2H), 7.7(d, 2H), 7.5–7.35(4H), 7.1(t, 1H), 4.5(t, 2H), 3.5(m, 1H), 2.0–1.1(27H), 1.0–0.8(6H)
② IR(KBr, cm⁻¹): 2910, 1740, 1670, 1605, 1280, 760
③ Mass: 574(M+)

3-fluoro-4-(2-methylnonanoyl) phenyl-4'-nonylbiphenyl-4-carboxylic acid ester

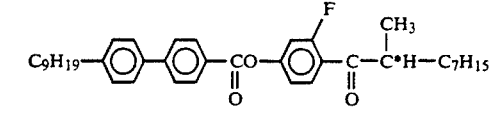

① ¹H-NMR (in CDCl₃, TMS standard, ppm): 8.25(d, 2H), 7.9(t, 1H), 7.75(d, 2H), 7.6(d, 2H), 7.35(d, 2H), 7.15(t, 2H), 3.4(m, 1H), 2.7(t, 2H), 1.9–1.2(31H), 0.9(6H)
② IR(KBr, cm⁻¹) 2910, 1730, 1680, 1605, 1270, 760
③ Mass: 572(M+)

3-fluoro-4-(2 methylnonanoyl) phenyl-4'-hexylbiphenyl 4-carboxylic acid ester

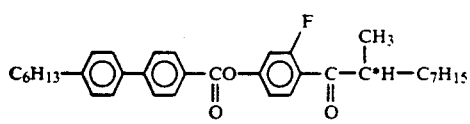

① ¹H-NMR (in CDCl₃, TMS standard, ppm): 8.25(d, 2H), 7.9(t, 1H), 7.7(d, 2H), 7.6(d, 2H), 7.4 7.0(4H), 3.35(m, 1H), 2.7(t, 2H), 2.0–1.1(23H), 1.0–0.8(6H)
② IR(KBr, cm⁻¹): 2920, 1730, 1680, 1605, 1230, 760
③ Mass: 530(M+)

3-fluoro-4-(2 methylnonanoyl) phenyl-4'-octyloxybiphenyl-4-carboxylic acid ester

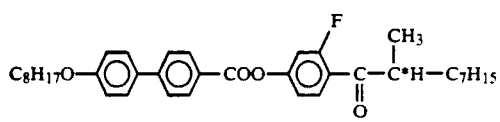

① ¹H-NMR (in CDCl₃, TMS standard, ppm): 8.25(d, 2H), 7.9(t, 1H), 7.75(d, 2H), 7.65(d, 2H), 7.1–7.2(2H), 7.05(d, 2H), 4.05(t, 2H), 3.35(m, 1H), 2.0–1.2(27H), 1.0–0.8(6H)
② IR(KBr, cm⁻¹): 2910, 1730, 1680, 1605, 1280, 760
③ Mass: 574(M+)

3-fluoro-4-(2-methyloctanoyl) phenyl 3-fluoro-4-heptyloxy benzoic acid

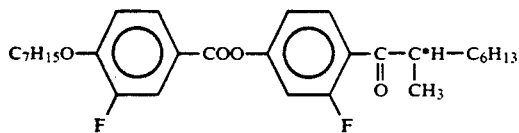

① ¹H-NMR (in CDCl₃, TMS standard, ppm): 8.1–7.8(3H), 7.3–6.9(3H), 4.15(t, 2H), 3.3(m, 1H), 2.1–1.1(23H), 1.1–0.8(6H)
② IR(KBr, cm⁻¹): 2920, 1730, 1680, 1610, 1510, 1285, 970, 750
③ Mass: 488(M+)

3-fluoro-4-(2-methylnonanoyl)phenyl-3-fluoro-4-hexyloxy benzoic acid

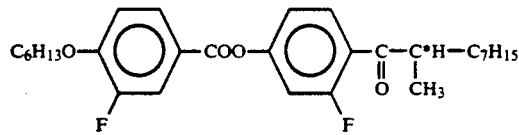

① ¹H-NMR (in CDCl₃, TMS standard, ppm): 8.05–7.8(3H), (3H), 4.15(t, 2H), 3.4(m, 1H), 2.0–1.1(23H),
② R(KBr, cm⁻¹): 2920, 1730, 1680, 1610, 1510, 1285, 970, 750
③ Mass: 488(M+)

3-fluoro-4-(2-methylnonanoyl) phenyl-3-fluoro-4-benzoic acid

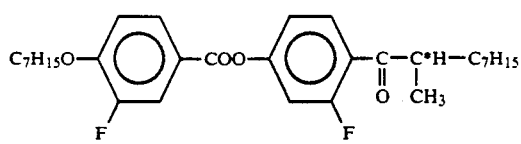

① ¹H-NMR (in CDCl₃, TMS standard, ppm): 8.0–7.8(3H), 7.15–7.0(3H), 4.15(t, 2H), 3.3(m, 1H), 2.0–1.1(25H), 1.1–0.8(6H)
② IR(KBr, cm⁻¹): 2920, 1730, 1680, 1610, 1285, 970, 750
③ Mass: 502(M+)

3-fluoro-4-(2-methylnonanoyl) phenyl 3-fluoro-4-octyloxy benzoic acid

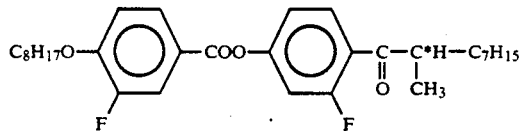

① ¹H-NMR (in CDCl₃, TMS standard, ppm): 8.0–7.8(3H), 7.15–7.0(3H), 4.1(t, 2H), 3.3(m, 1H), 2.0–1.8(3H), 1.6–1.2(24H), 1.1–0.8(6H)
② IR(KBr, cm⁻¹): 2920, 1730, 1680, 1610, 1285, 1235, 970, 750
③ Mass: 516(M+)

3-fluoro-4-(2-methylnonanoyl) phenyl-3-fluoro-4-nonyloxy benzoic acid

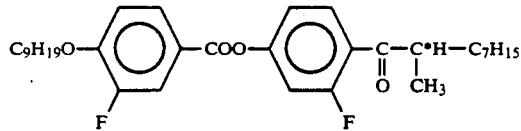

① ¹H-NMR (in CDCl₃, TMS standard, ppm): 8.0–7.85(3H), 7.15–7.0(3H), 4.15(t, 2H), 3.3(m, 1H), 2.0–1.1(29H), 1.0–0.9(6H)
② IR(KBr, cm⁻¹) 2920, 1730, 1680, 1610, 1285, 1235, 970, 750
③ Mass: 530(M+)

3-fluoro-4-(2-methylnonanoyl) phenyl-3-fluoro-4-decyloxy benzoic acid

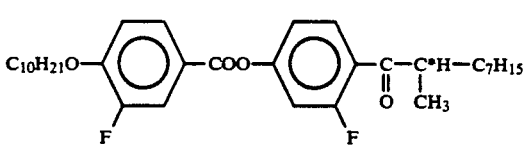

① ¹H-NMR (in CDCl₃, TMS standard, ppm): 8.0–7.85(3H), 7.15–7.0(3H), 4.15(t, 2H), 3.3(m, 1H), 2.0–1.8(m, 3H), 1.6–1.2(28H), 1.0–0.8(6H)
② IR(KBr, cm⁻¹): 2920, 1730, 1680, 1610, 1290, 1115, 970, 750
③ Mass: 544(M+)

3-fluoro 4-(2-methylnonanoyl) phenyl-3'-fluoro-4'-octyloxybiphenyl-4'-carboxylic acid

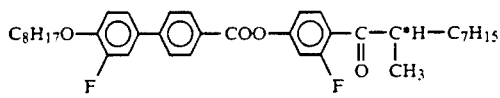

① $^1$H-NMR (in CDCl$_3$, TMS standard, ppm): 8.25(d, 2H), 7.9(t, 1H), 7.7(d, 2H), 7.4(t, 2H), 7.2-7.0(3H), 4.1(t, 2H), 3.3(m, 1H), 1.9-1.2(26H), 0.9(6H)

② IR(KBr, cm$^{-1}$): 2920, 1730, 1675, 1605, 1500, 1230

③ Mass: 592(M+)

Moreover, the length of the alkyl chain of R in the compound shown by the formula (I) can properly be selected in accordance with the use purpose likewise the case of the alkyl chain in the above intermediate because this compound affects the temperature region and the like forming a liquid crystal state. Of course, such compounds may be used alone or in admixture with the other liquid crystal material.

The compound of the general formula (I) and the intermediate of the general formula (II) can be synthesized through the following steps.

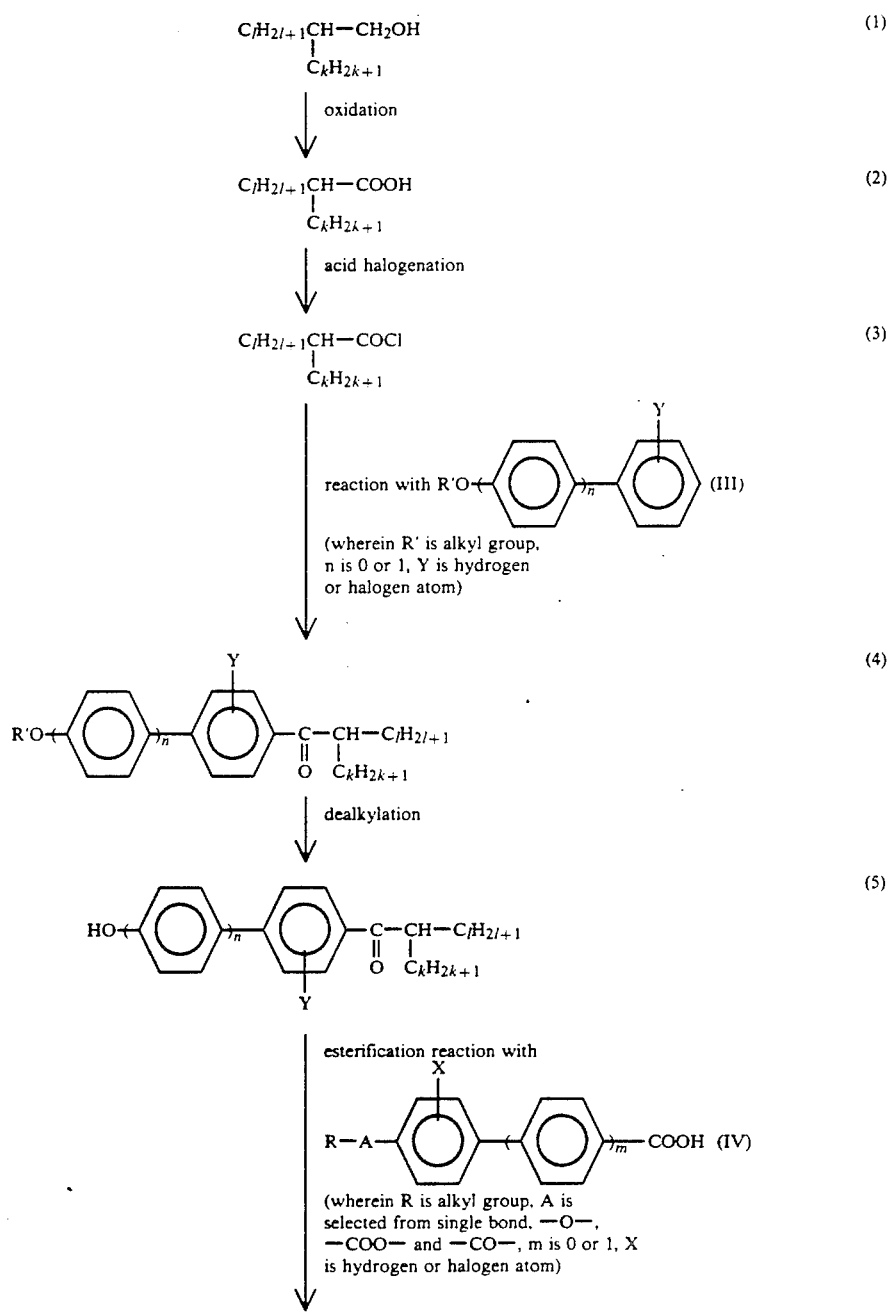

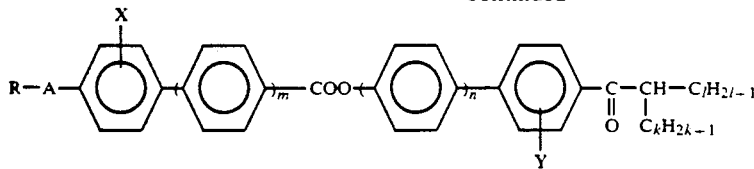

At first, 2-alkyl-1-alkanol (1) is used as a starting material, which is oxidized with an oxidizing agent. In order to obtain a compound having an optical activity, 2-alkyl-1-alkanol having an optical activity is sufficient t be used as a starting material. In the latter case, an oxidizing agent capable of performing oxidation without racemization is selected. Such an oxidation is most convenient to be carried out by using potassium permanganate under an acidity.

Then, the thus obtained 2-alkyl-1-alkylcarboxylic acid (2) is reacted with an inorganic halide such as thionyl chloride, phosphorus pentachloride, phosphorus trichloride, phosphorylchloride or the like to form an acid halide (3).

The acid halide is reacted with the compound of the above formula (III) in the presence of a catalyst such as anhydrous aluminum chloride, boron trifluoride or the like according to Friedel-Crafts reaction to obtain a corresponding keto compound (4).

Then, the compound (4) is reacted with an anhydrous aluminum bromide or the like to conduct dealkylation, whereby a corresponding phenol compound (5) is obtained.

Thereafter, the compound (5) is esterified with a compound of the above formula (Y), whereby a compound (6) can be obtained without racemization even in case of compounds having an optical activity.

When the compound (5) is particularly fluoro-4-(2-alkylalkanoyl) phenol represented by the following general formula (II):

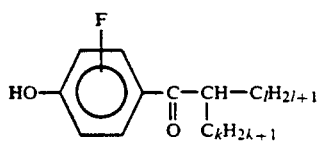

(in which k and l are the same as mentioned above), the concrete production method is as follows.

At first, 2-alkyl-1-alkylalcohol is oxidized with an oxidizing agent. As the oxidizing agent, substances capable of performing oxidation without racemization are selected in case of the synthesis of optically active compounds, among which potassium permanganate is most convenient and preferable. The oxidation reaction using potassium permanganate is preferably carried out under an acidity. In this case, sulfuric acid is used as an acid. On the other hand, the oxidation of short alkyl chain, for example, 2-methyl butanol is promoted under an alkaline condition without racemization. In the latter case, sodium hydroxide is cheap and convenient as an alkali agent. According to this reaction operation, 2-alkyl 1-alkanol is added to an aqueous solution of 2-50% sulfuric acid and then potassium permanganate is slowly added thereto in an amount of 1-3 times per 1 mol of alcohol while maintaining temperature at 20°-30° C. Then, the thus obtained reaction mixture is added to an aqueous solution of sodium bisulfite, whereby unreacted potassium permanganate and manganese dioxide are dissolved in water, so that the resulting product can be extracted with an organic solvent such as ether or the like. After the repetition of such an extraction, 2-alkyl-1-alkyl carboxylic acid can be isolated and purified by the conventionally known means such as distillation, column chromatography or the like.

The thus obtained 2-alkyl-1-alkyl carboxylic acid is reacted with an inorganic halide such as thionyl chloride, phosphorus pentachloride, phosphorus trichloride, phosphoryl chloride or the like to form an acid halide.

This reaction operation is carried out by holding the 2-alkyl-1-alkyl carboxylic acid at a temperature of 20°-60° C., dropwise adding the inorganic halide and reacting them at a temperature of 50°-90° C. for 1-3 hours.

The thus obtained acid halide is reacted with o-or m-fluoroanisole in the presence of anhydrous aluminum chloride to produce fluoro-4-(2-alkylalkanoyl) anisole without racemization even in case of compounds having an optical activity. In such an acylation operation, the acid halide is dissolved in an organic solvent such as methylene chloride or the like, and anhydrous aluminum chloride is added thereto while holding temperature at $-5°$ C.$-+5°$ C. to form a complex, and then anisole dissolved in an organic solvent such as methylene chloride or the like is added dropwise to the complex while holding temperature at $-10°$ C.$-+10°$ C. and reacted for 1-10 hours, whereby fluoro-4-(2-alkylalkanoyl) anisole can be obtained.

The above fluoro-4-(2-alkylalkanoyl) anisole is reacted with anhydrous aluminum bromide, boron trifluoride, phosphorus tribromide or the like at room temperature in an organic solvent such as toluene or the like, whereby fluoro-4-(2-alkylalkanoyl) phenol of the above formula (II) can be obtained.

Moreover, the compound of the above formula (III) can be obtained by the following method. When Y in the formula is a hydrogen atom, commercially available phenol or p-phenyl phenol is reacted with an alkyl halide. Alternatively, commercially available anisole or 4-methoxy biphenyl may be used.

On the other hand, when Y in the formula is a halogen atom, if n is 1, compounds are easily obtained by coupling p-iodoanisole with chloro or fluoro iodobenzene. Further, if n is 0, compounds are obtained by reacting chloro or fluoro phenol with an alkyl halide. Alternatively, commercially available chloroanisole or fluoroanisole may be used.

Then, the compounds of the above formula (IV) can be obtained by the following method.

When X of the above formula is a hydrogen atom, compounds are obtained according to the following reaction course:

m = 0:

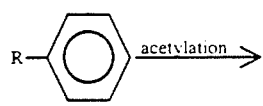
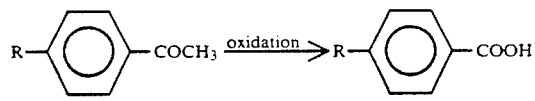
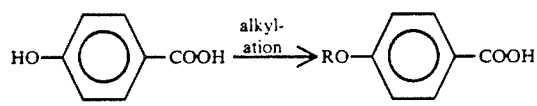
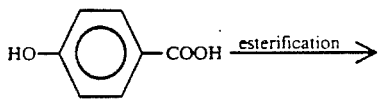
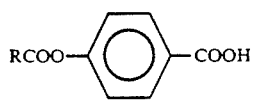
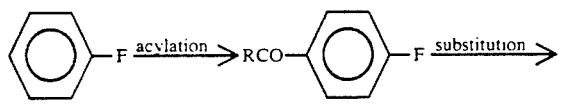
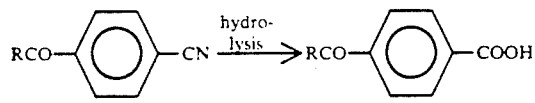
m = 1:
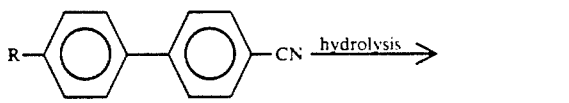
m = 0:
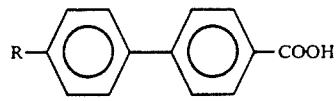
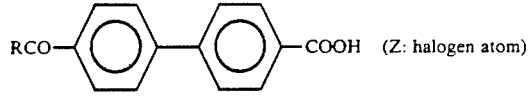
(Z: halogen atom)
On the other hand, when X of the above formula is a halogen atom, compounds are obtained according to the following reaction course:
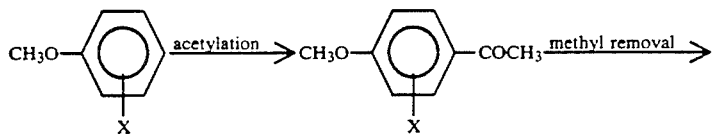
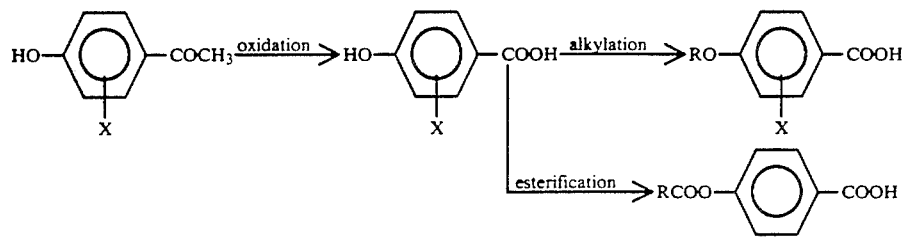

-continued
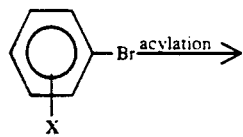
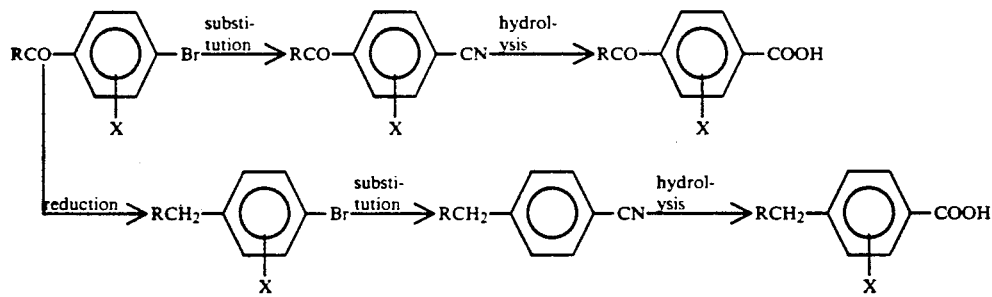
$m = 1$:
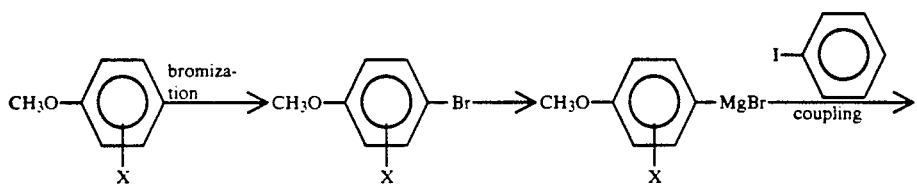
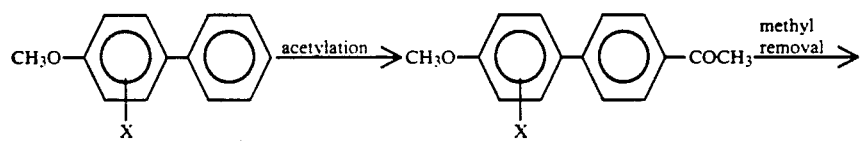
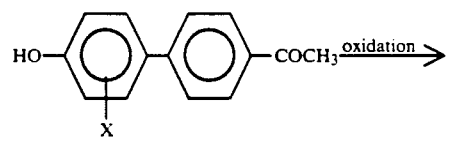
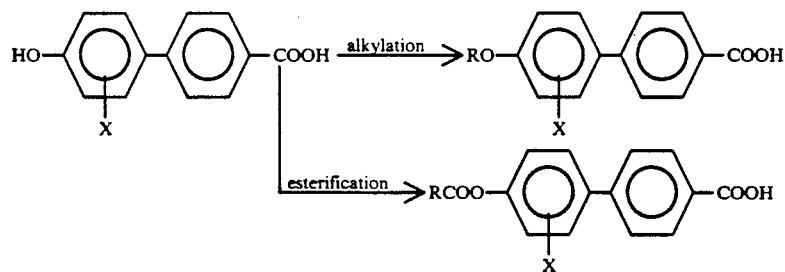
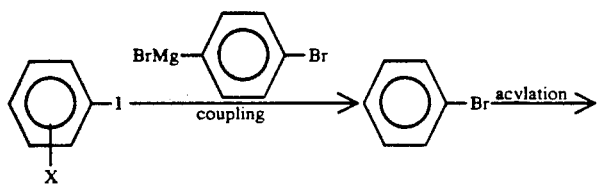

-continued

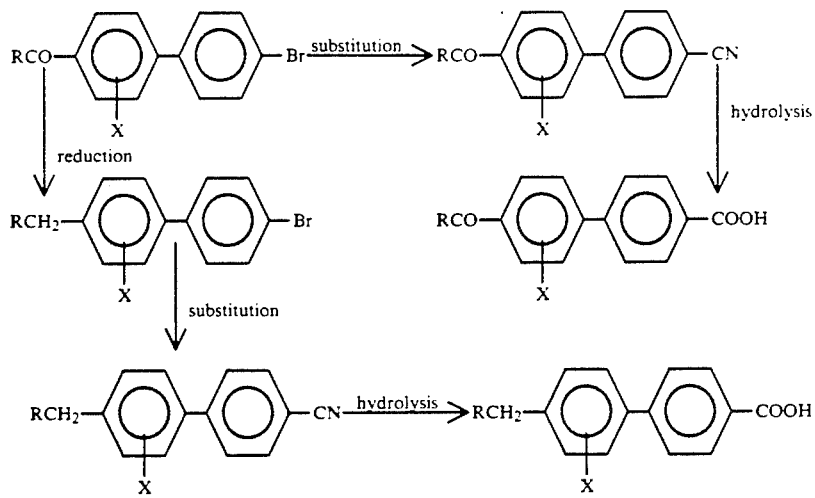

The following examples are given in illustration of the invention and are not intended as limitations thereof.

EXAMPLE 1

2-fluoro-4-(2-methyloctanoyl) phenyl-4′-octyloxybiphenyl-4-carboxylic acid ester Synthesis of (+)-2-fluoro-4-(2-methyloctanoyl) phenol After 46.4 g of concentrated sulfuric acid and 21.2 g (147 mmol) of (-)-2-methyloctanol were added to 330 ml of water, 63.4 g (401 mmol) of potassium permanganate was added dropwise over 7.3 hours while holding a reaction temperature at 21°-28° C. The thus obtained reaction mixture was poured into 270 ml of ice water, and 52 g of sodium bisulfite was added thereto. After pH was adjusted to not more than 1 with hydrochloric acid, the resulting product was extracted with ether and further with a 10% aqueous solution of sodium hydroxide. The extract was added with hydrochloric acid to adjust pH to not more than 1 and again extracted with chloroform. The thus obtained extract was washed with water, dried, concentrated and then distilled under a reduced pressure (0.28 mmHg, 91°-94° C.) to obtain 15.3 g (yield: 64%) of (+)-2-methyl octanoic acid.

To 8.98 g (75.5 mmol) of thionyl chloride placed in a flask was added 8.93 g (56.4 mmol) of the above (+)-2-methyl octanoic acid with stirring at room temperature. Then, the mixture was stirred and reacted at room temperature for 10 minutes, at 30° C. for 20 minutes, at 40° C. for 30 minutes and at 70° C. for 2 hours. Thereafter, an excessive amount of thionyl chloride was distilled off to obtain 9.80 g (55.5 mmol, yield: 98%) of a light brown (+)-2-methyl octanoic acid chloride.

Then, 2.20 g (11.4 mmol) of the above (+)-2-methyl octanoic acid chloride was added with 1 ml of dried methylene chloride, to which was added dropwise 1.70 g (12.8 mmol) of anhydrous aluminum chloride under ice water cooling over 8 minutes. The resulting mixture was further stirred on an ice water bath to change into a light yellow solution.

Separately, 1.38 g (10.9 mmol) of o-fluoroanisole and 2 ml of dried methylene chloride were placed into a flask and stirred while cooling on an ice water bath. To this mixture was added dropwise the aforementioned complex solution of acid chloride and anhydrous aluminum chloride together with 0.5 ml of dried methylene chloride over 4 minutes to obtain a light reddish brown solution. Thereafter, this solution was stirred while cooling on the ice water bath for 40 minutes and further at room temperature for 2 hours. Then, the solution was poured into 100 ml of ice water together with 40 ml of methylene chloride to conduct two-layer separation. After the extraction with methylene chloride was carried out, the extract was washed with water and dried on magnesium sulfate. After magnesium sulfate was filtered off, the filtrate was concentrated and dried under a reduced pressure to obtain 2.9 g of a light brown oil.

After this oil was isolated and purified by a column chromatography (silica gel/toluene), a fraction containing only an objective compound was concentrated and azeotropically distilled together with toluene to remove the remaining 2-fluoroanisole, and then the residue was dried under a reduced pressure to obtain 2.10 g (7.88 mmol, yield: 72%) of a colorless and transparent liquid of (+)-2-fluoro-4-(2-methyloctanoyl) anisole.

Next, 2.00 g (7.51 mmol) of the above (+)-2-fluoro-4-(2-methyloctanoyl) anisole and 35 ml of dried toluene were placed in a flask and stirred while cooling on an ice water bath, to which was added dropwise 4.1 g (15.4 mmol) of anhydrous aluminum bromide over 2 minutes to obtain a light reddish and transparent solution. This solution was further stirred while cooling on the ice water bath. About 15 minutes after the further stirring, the precipitation of a white crystal was started and the whole of the solution was cloudy after 2 hours and the stirring became impossible. After the solution was reacted on the ice water bath for about 2.3 hours, the temperature was raised to room temperature, and this temperature was held for about 15 hours. The resulting reaction mixed solution was poured into 150 ml of ice water together with 30 ml of toluene. After the separation into two layers, the extraction with 30 ml of toluene on aqueous layer was repeated two times. The extracts were gathered with organic layer, which was washed with 50 ml of water and dried on magnesium sulfate. After magnesium sulfate was filtered off, the filtrate was concentrated and dried under a reduced pressure to obtain 1.9 g (7.5 mmol, yield: about 100%) of a light red oil of (+) 2-fluoro-4-(2-methyloctanoyl) phenol having the aforementioned physical and chemical properties.

Synthesis of 4'-octyloxybiphenyl-4-carboxylic acid

To a solution of 50 g of sodium hydroxide in 240 ml of a mixed solvent of water and ethanol was added 10 g (32 mmol) of commercially available 4'-octyloxy-4-cyanobiphenyl, which was heated and reacted under reflux for 3 hours. The reaction mixture was acidified with hydrochloric acid, filtered off and recrystallized with a mixed solvent of ethanol and acetic acid to obtain a solid. As a result of an infrared spectrum analysis of this solid product by KBr process, absorptions were recognized at 3400 cm$^{-1}$, 3200 cm$^{-1}$, 2950-2850 cm$^{-1}$, 650 cm$^{-1}$ and 1600, cm$^{-1}$ respectively, from which it was confirmed to be 4'-octyloxybiphenyl 4-carboxylic acid.

Synthesis of 2-fluoro-4-(2-methyloctanoyl) phenyl-4'-octyloxybiphenyl-4-carboxylic acid ester Into a flask of 50 ml were charged 294 mg (1.16 mmol) of the above (+)-2-fluoro-4-(2-methyloctanoyl) phenol, 385 mg (1.18 mmol) of the above 4'-octyloxybiphenyl-4-carboxylic acid and 20 ml of dried methylene chloride, which were suspended with stirring. To the resulting suspension were added 16.8 mg (0.14 mmol) of N,N-dimethylamino pyridine and 258 mg (1.25 mmol) of dicyclohexyl carbodiimide (DCC), which were heated under reflux for 5.5 hours. After air cooling up to room temperature, the precipitated white crystal was filtered, and the filtrate was concentrated and dried under a reduced pressure to obtain 0.69 g of a reddish brown crystal.

This crystal was isolated and purified by a column chromatography (silica gel/toluene) to obtain 0.13 g (0.23 mmol, yield: 20%) of a white crystal of 2-fluoro-4-(2-methyloctanoyl) phenyl-4'-octyloxybiphenyl- (4-carboxylic acid ester having the aforementioned physical and chemical properties.

Evaluation of liquid crystal properties

As a result that the change of texture of the above compound was observed by means of a polarized microscope provided with a hot stage, it was a liquid crystal state of smectic A phase at 87° C. and finally an isotropic liquid at 121° C. during the heating. On the other hand, during the cooling, it was a liquid crystal state of smectic A phase at 121° C., changed into a liquid crystal of chiralsmectic C phase at 73° C. and was finally a solid crystal at 57° C.

After the above compound was placed in a 3 μm thick cell having ITO deposited glass plates with rubbed polyimide films, the spontaneous polarization was measured by a triangle wave method, and consequently the compound showed a large spontaneous polarization of 109 nC/cm$^2$ at 60° C.

EXAMPLE 2

2-fluoro-4-(2-methyloctanoyl) phenyl-4-octyloxy benzoic acid ester

Synthesis of 4-octyloxy benzoic acid

Into a flask of 500 ml were charged 15.6 g of sodium hydroxide, 80 ml of water and 160 ml of ethanol, to which was added and dissolved 24.8 g (0.18 mmol) of 4-hydroxy benzoic acid. Then, the resulting mixture was added with 37.1 g (0.18 mmol) of bromooctane and heated under reflux for 4 hours with stirring. The reaction mixture was cooled and added with hydrochloric acid to adjust pH to not more than 2, whereby a solid was precipitated, filtered and recrystallized with ethyl alcohol to obtain 41.9 g of a white solid. As a result of an infrared spectrum analysis of this product by KBr process, absorptions were recognized at 1675 cm$^{-1}$ and 1600 cm$^{-1}$, respectively, from which it was confirmed to be 4-octyloxy benzoic acid.

Synthesis of 2-fluoro-4-(2-methyloctanoyl) phenyl-4-octyloxy benzoic acid ester

Into a flask of 50 ml were charged 293 mg (1.11 mmol) of (+)-2-fluoro-4-(2-methyloctanoyl) phenol obtained in the same manner as in Example 1, 303 mg (1.21 mmol) of the above 4 octyloxy benzoic acid and 4 ml of dried methylene chloride, which was slightly heated to form a homogeneous solution. When 16.5 mg (0.14 mmol) of N,N-dimethylamino pyridine and 252 mg (1.22 mmol) of DCC were added to the solution, a white crystal was precipitated immediately. The resulting mixture was stirred at room temperature for about 1.3 hours, heated under reflux for about 15 minutes and air cooled.

After the resulting white crystal was filtered with methylene chloride, the filtrate was washed with 20 ml of an aqueous solution of 2 normal hydrochloric acid, 20 ml of an aqueous solution of 1 normal sodium hydroxide and 20 ml of water in this order, and then dried on magnesium sulfate. After magnesium sulfate was filtered off, the filtrate was concentrated and dried to obtain 0.57 g of oil and crystal.

The oil and crystal were isolated and purified by column chromatography (silica gel/toluene) to obtain 0.41 g (0.85 mmol, yield: 75%) of a slightly brown crystal of 2-fluoro-4-(2-methyloctanoyl) phenyl-4-octyloxy benzoic acid ester having the aforementioned physical and chemical properties.

Evaluation of liquid crystal properties

As a result of the same observation as in Example 1, the above compound changed from the crystal into an isotropic liquid at 33° C. during the heating. On the other hand, it was a liquid crystal state of smectic A phase at −3° C. and was finally crystallized at −8° C. during the cooling.

After the compound was placed in a 3 μm thick cell having ITO deposited glass plates with rubbed polyimide films, when a voltage was applied, the electroclinic effect was observed at the smectic A phase.

EXAMPLE 3

2-fluoro-4-(2-methyloctanoyl) phenyl-4-decanoyloxy benzoic acid ester

Synthesis of 4-decanoyloxy benzoic acid

To a solution of 5.0 g (40 mmol) of p-hydroxy benzoic acid in 40 ml of pyridine was added dropwise 7.0 g (40 mmol) of decanoic acid chloride in 10 minutes. The resulting mixed solution was reacted at room temperature for 5 hours with stirring, cooled on ice and added with an aqueous solution of 6 normal hydrochloric acid to adjust pH to not more than 2.

The precipitated solid was filtered and recrystallized with ethyl alcohol to obtain 8.6 g (yield: 94%) of a white solid of 4-decanoyloxy benzoic acid having an absorption at 1706 cm$^{-1}$ through an infrared spectrum analysis.

Synthesis of 2-fluoro-4-(2-methyloctanoyl) phenyl-4-decanoyloxy benzoic acid ester Into a flask of 50 ml were charged 292 mg (1.16 mmol) of (+)-2-fluoro-4-(2-methyloctanoyl) phenol obtained in the same manner as in Example 1, 5 ml of dried methylene chloride, 345 mg (1.18 mmol) of the above 4-decanoyloxy benzoic acid and 16.5 mg (0.14 mmol) of N,N-dimethylamino pyridine, which were stirred at room temperature to form a homogeneous solution. When 252 mg (1.22 mmol) of DCC was added to the above solution, a whitecrystal was immediately precipitated. After the stirring was continued at room temperature for 2.5 hours, the precipitated white crystal was filtered off, and then the filtrate was concentrated and dried to obtain a light reddish brown crystal.

The above crystal was isolated and purified by a column chromatography (silica gel/toluene) to obtain 0.34 g (yield: 56%) of a white crystal of 2-fluoro 4-(2-methyloctanoyl) phenyl 4-decanoyloxy benzoic acid ester having the aforementioned physical and chemical properties.

EXAMPLE 4

2-fluoro-4-(2-methyloctanoyl phenyl-4-nonanoyl benzoic acid ester

Synthesis of 4-nonanoyl benzoic acid 188.7 g (1.413 mol) of anhydrous aluminum chloride was added to 566 ml of 1,2-dichloro ethane, to which was added dropwise 161.5 g (1.682 mol) of benzene fluoride while holding temperature at 3°-5° C. The resulting mixture was added with 254.5 g (1.442 mol) of nonanoyl chloride over 2 hours and then reacted at 8° C. for 1 hour and at 8°-30° C. for 5 hours. The reaction solution was poured into 600 ml of concentrated hydrochloric acid containing 200 g of ice and extracted with 1.5 l of chloroform. The extract was washed with water and a 5% solution of sodium carbonate and dried on magnesium sulfate. After the solvent was distilled off, the residue was distilled under a reduced pressure (145°-150° C./5 mmHg) to obtain 292.2 g (yield: 86%) of 4-nonanoyl-benzene fluoride.

To 1350 ml of dimethylsulfoxide were added 292.2 g (1.238 mol) of the above 4-nonanoyl-benzene fluoride and 67.4 g (1.374 mol) of sodium cyanide, which were reacted at 110°-125° C. for 12 hours. After the cooling up to room temperature, the reaction solution was poured into 2.7 l of water and extracted with 2 l of chloroform. The extract was washed with a saturated saline solution and dried on anhydrous magnesium sulfate. The solvent was distilled off to obtain 317.9 g (yield: 100%) of brown oily substance of 4-nonanoyl benzonitrile having an infrared absorption spectrum of 1680 cm$^{-1}$.

Then, 314.1 g of the above 4-nonanoyl benzonitrile was added to 314 ml of ethyl alcohol, warmed to 80°-82° C., added dropwise with 1500 ml of 30% potassium hydroxide and then reacted under reflux for 5 hours. After 1.5 l of water was added to the reaction solution, the precipitated solid was filtered, washed with methyl alcohol and air dried to obtain 283.1 g of a light brown crystal. This crystal was added to a solution of 200 ml of concentrated hydrochloric acid in 1.5 l of water, heated at 65°-82° C. for 1 hour with stirring and filtered. Further, the solid was added to a solution of 200 ml of concentrated hydrochloric acid in 1100 ml of acetic acid, warmed and dissolved, cooled to 30° C., filtered, washed with acetic acid, water and methyl alcohol in this order and air dried to obtain 170 g (yield: 50%) of 4-nonanoyl benzoic acid having the following properties:

① $^1$H-NMR (in CDI$_3$-CF$_3$CO$_2$D, TMS standard, δ ppm): 11.4(s, 1H), 8.2–8.0(AB$_q$, 4H), 3.1(t, 2H), 2.1–1-1.1(m, 12H), 0.9(t, 3H)

② IR (KBr, cm$^{-1}$): 1680

Synthesis of 2-fluoro-4-(2-methyloctanoyl) phenyl-4-nonanoyl benzoic acid ester

Into a flask of 50 ml were charged 321 mg (1.22 mmol) of the above 4-nonanoyl benzoic acid, 293 mg (1.16 mmol) of (+)-2-fluoro-4-(2-methyloctanoyl) phenol obtained in the same manner as in Example 1, 17.0 mg (0.14 mmol) of N,N dimethylamino pyridine and 20 ml of dried methylene chloride, which were heated with stirring to form a homogeneous solution. The resulting solution was added with 226 mg (1.10 mmol) of DCC and further heated with stirring for about 1 hour. After air cooling, the precipitated crystal was filtered off, and then the filtrate was concentrated and dried under a reduced pressure to obtain a white crystal.

This crystal was purified by a column chromatography (silica gel/toluene}to obtain 0.50 g (1.0 mmol, yield: 90%) of a white crystal of 2-fluoro-4-(2-methyloctanoyl) phenyl-4-nonanoyl benzoic acid ester having the aforementioned physical and chemical properties.

EXAMPLE 5

4-2-(methyloctanoyl) phenyl-3-chloro-4-octyloxy benzoic acid ester

Synthesis of 3-chloro-4-octyloxy benzoic acid

Into a flask was charged 2.4 g (59 mmol) of sodium hydroxide, which was dissolved in 6 ml of water. In the resulting solution was uniformly dissolved 5.0 g (28 mmol) of 3-chloro-4-hydroxy benzoic acid, to which was added dropwise 5.3 g (28 mmol) of octyl bromide over 10 minutes. Thereafter, the mixture was stirred under reflux for 10 hours. After the completion of the reaction, ethanol was distilled off, and the residue was added with an aqueous solution of 6 normal hydrochloric acid to adjust pH<2 while cooling on ice, whereby about 2.0 g of a solid was precipitated and filtered off. Then, the solid was recrystallized with ethanol to obtain 1.5 g (yield: 18%) of a white needle crystal of 3-chloro-4-octyloxy benzoic acid having the following properties:
IR (KBr, cm$^{-1}$): 2800, 2700, 1680, 1590

Synthesis of (+)-4-(2-methyloctanoyl) phenol

Into a flask of 10 ml were charged 2.03 g (11.5 mmol) of 2-methyl octanoic acid chloride obtained in the same manner as in Example 1 and 3.0 ml of dried methylene chloride, to which was added 1.75 g of anhydrous aluminum chloride with stirring at room temperature and dissolved thereinto with further stirring. The resulting solution was added dropwise to a mixture of 1.23 g (11.3 mmol) of dried anisole and 3.0 ml of dried methylene chloride with stirring while cooling on ice at a reaction temperature of not higher than 6° C., which was further stirred for 30 minutes. Thereafter, the mixture was stirred at room temperature over a night.

Then, the reaction mixture was poured into 100 ml of ice water, extracted with 25 ml of methylene chloride twice. The organic layer was washed with 40 ml of water and dried on magnesium sulfate. After the filtration and concentration, the product was isolated and purified by a column chromatography using silica gel to obtain 1.84 g (7.4 mmol, yield: 65%) of a yellowish brown oily substance of (+)-4-(2-methyloctanoyl) anisole.

Into a flask of 50 ml were charged 1.84 g (7.4 mmol) of the above 4-(2-methyloctanoyl) anisole and 35 ml of dried toluene, and 8.68 g of anhydrous aluminum bromide was added thereto with stirring under ice cooling, which were then stirred at room temperature over a night. Thereafter, the mixture was stirred at 40° C. for 4 hours, air cooled and poured into 100 ml of ice water. After the extraction with 40 ml of toluene was repeated two times, the organic layer was washed with 80 ml of water and dried on magnesium sulfate. After the filtration and concentration, the product was dried under a reduced pressure to obtain 1.70 g (7.3 mmol, yield: 98%) of a reddish brown oily (+)-4-(2-methyloctanoyl) phenol having the following properties:

① $^1$H-NMR (in CDCl$_3$, TMS standard, ppm): 8.2–7.9(broad, 1H), 8.0(AB$_1$, 2H), 7.0(AB$_q$, 2H), 3.4(m, 1H), 1.9–1.2(m, 17H), 0.9(t, 3H)
② IR (KBr, cm$^{-1}$) 3250, 1650, 1580
③ Mass: 262(M+)
④ $[\alpha]^{25}_D$: +22.70°

Synthesis of 4-(2-methyloctanoyl) phenyl-3-chloro-4-octyloxy benzoic acid ester

Into a flask of 50 ml were charged 500 mg (1.8 mmol) of the above 3-chloro-4-octyloxy benzoic acid, 420 mg (1.8 mmol) of the above (+)-4-(2-methyloctanoyl) phenol, 390 mg (1.9 mmol) of DCC and 9 mg of dimethylamino pyridine, and 10 ml of anhydrous methylene chloride was added thereto, which were then stirred under reflux for 8 hours. After the completion of the reaction, the precipitated solid was filtered off, and the resulting filtrate was washed with 20 ml of an aqueous solution of 1 normal hydrochloric acid and further with 20 ml of water. After the solvent was distilled off, the residue was concentrated. Then, the residue was purified through a silica gel column [toluene:hexane=2:1 (v/v)], dissolved in a small amount of ethanol to conduct recrystallization. Further, the precipitated solid was filtered off and again recrystallized. This procedure was repeated two times to obtain 75 mg (yield: 8%) of a white solid having the aforementioned physical and chemical properties.

Evaluation of liquid crystal properties

As a result of the same observation as in Example 1, the above compound changed from the crystal into an isotropic liquid at 33.5° C. during the heating. On the other hand, it was a liquid crystal state of smectic A phase at 11.7° C. and was finally crystallized at −27.3° C. during the cooling.

When a voltage was applied in the same manner as in Example 2, the electroclinic effect was observed at the smectic A phase.

EXAMPLE 6

4′-(2-methyloctanoyl) biphenyl-3-chloro-4-octyloxy benzoic acid ester

Synthesis of 4-hydroxy 4′-(2-methyloctanoyl) biphenyl

Into a flask was charged 1.0 g (5.4 mmol) of commercially available 4-methoxy biphenyl, which was dissolved into 3 ml of nitrobenzene in a nitrogen atmosphere. To the resulting solution was added dropwise a mixture of 1.5 g (8.1 mmol) of (+)-2-methyloctanoyl chloride obtained in the same manner as in Example 1 and 2.2 g (8.1 mmol) of aluminum bromide, which was previously stirred under ice cooling, at room temperature for 5 minutes. After the completion of the addition, the temperature inside the reaction vessel was raised to 40° C., and the stirring was continued at this temperature for about 9 hours and further at room temperature over a night. After the completion of the reaction, the reaction solution was poured into 50 ml of ice water of pH=1 together with 25 ml of chloroform. After the separation into two layers, only the organic layer was taken out and the extraction with 40 ml of chloroform on aqueous layer was repeated three times. Thereafter, the organic layers were gathered, washed with 50 ml of water four times and dried on anhydrous magnesium sulfate. After magnesium sulfate was filtered off, the product was concentrated, purified through a silica gel column [hexane→hexane:toluene=1:1 (v/v)] and recrystallized with ethanol to obtain 430 mg (yield: 25%) of a white solid of 4-methoxy-4′-(2-methyloctanoyl) biphenyl having the following properties:

① $^1$H-NMR (in CDCl$_3$, TMS standard, ppm): 8.05(d, 2H), 7.64(d, 2H), 7.58(d, 2H), 6.92(d, 2H), 3.82(s, 3H), 3.50(m, 1H), 1.90–0.80(m, 16H)
② IR (KBr, cm$^{-1}$): 2920, 2700, 1670, 1600

Then, 400 mg (1.2 mmol) of the above 4-methoxy-4′-(2-methyloctanoyl) biphenyl was dissolved in 6 ml of dried toluene in a flask of 50 ml. After the solution was added with 1.3 g (5.0 mmol) of aluminum bromide under ice cooling for 5 minutes, the resulting mixture was stirred under ice cooling for 6 hours, at room temperature for about 60 hours and at 40° C. for 11 hours. After the completion of the reaction, the resulting product was poured into 100 ml of ice water together with 40 ml of toluene. After the separation into two layers, the organic layer was taken out, and the extraction with 40 ml of toluene on aqueous layer was repeated two times. Thereafter, the organic layers were gathered, washed with 40 ml of water and dried on anhydrous magnesium sulfate. After magnesium sulfate was filtered off, the product was concentrated and purified through a silica gel column (toluene→toluene: diethyl ether=5:1 (v/v)] to obtain 200 mg (yield: 54%) of a reddish brown oily substance of 4-hydroxy-4′-(2-methyloctanoyl) biphenyl having the following properties:

① $^1$H-NMR (in CDCl$_3$, TMS standard, ppm): 7.98(d, 2H), 7.60(d, 2H), 7.50(d, 2H), 6.92(d, 2H), 3.48(m, 1H), 2.00–0.75(m, 16H)
② IR (KBr, cm$^{-1}$): 3600, 2700, 1756, 1590
③ $[\alpha]^{25}_D$: +6.0°(C 4.26)

Synthesis of 4′-(2-methyloctanoyl) biphenyl-3-chloro-4-octyloxy benzoic acid ester Into a flask of 50 ml were charged 80.1 mg (0.28 mmol) of 3-chloro-4-octyloxy benzoic acid obtained in the same manner as in Example 5, 83.4 m9 (0.27 mmol) of the above 4-hydroxy-4′-(2-methyloctanoyl) biphenyl, 61.1 mg (0.30 mmol) of DCC, 3.5 mg (0.03 mmol) of 4-dimethylamino pyridine and 5 ml of dried methylene chloride with stirring, and then heated under reflux for 5 hours. After the cooling, the precipitated solid was filtered off, and the filtrate was washed with 10 ml of methylene chloride two times. The obtained organic layers were gathered, and washed with 0.1 normal hydrochloric acid and further with water. After the drying on anhydrous magnesium sulfate and the distilling off of the solvent, the obtained rough crystal was purified through a silica gel column chromatography and recrystallized with ethanol to obtain 82.3 mg (yield: 53%) of a white crystal of 4'-(2-methyloctanoyl) biphenyl-3-chloro-4-octyloxy benzoic acid ester having the aforementioned physical and chemical properties.

Evaluation of liquid crystal properties

As a result of the same observation in Example 1, the above compound changed from an isotropic liquid into liquid crystal states of smectic A phase at 107.2° C. and chiralsmectic C phase at 86.0° C. and was finally crystallized at 43.2° C. during the cooling. On the other hand, during the heating, it changed from the crystal into a liquid crystal state of enantropically stable chiralsmectic C phase at 70.6° C.

The spontaneous polarization was measured in the same manner as in Example 1, and consequently the compound showed a large spontaneous polarization of 286 nC/cm$^2$ at 46° C.

EXAMPLE 7

4'-(2-methyloctanoyl) biphenyl-3-chloro-4-octylcarbonyloxy benzoic acid ester

Synthesis of 3-chloro-4-octylcarbonyloxy benzoic acid

To a solution of 2.0 g ($1.1 \times 10^{-2}$ mol) of 3-chloro-4-hydroxy benzoic acid in 40 ml of dried methylene chloride containing 3.0 g ($9.2 \times 10^{-3}$ mol) of pyridine was added dropwise 3.0 g ($9.2 \times 10^{-3}$ mol) of nonanoic acid chloride, which were stirred under reflux for 7 hours. After the completion of the reaction, the solution was washed with an aqueous solution of 1 normal hydrochloric acid and further with water and dried on anhydrous magnesium sulfate. After magnesium sulfate was filtered off, the resulting product was purified through a silica gel column chromatography using methylene chloride and ethanol at 9:1 (v/v) as a developing solution and then recrystallized with 5 ml of ethanol to obtain 750 mg (yield: 25%) of a white solid.

Synthesis of 4'-(2-methyloctanoyl) biphenyl-3-chloro 4-octylcarbonyloxy benzoic acid ester The same procedure as in Example 6 was repeated by using the above obtained 3-chloro-4-octylcarbonyloxy benzoic acid and 4-hydroxy-4'-(2 methyloctanoyl) biphenyl obtained in the same manner as in Example 6, and the resulting product was subjected to silica gel column chromatography and recrystallization to obtain 430 mg (yield: 31%) of a light brown solid of 4'-(2-methyloctanoyl) biphenyl-3-chloro-4-octylcarbonyloxy benzoic acid ester having the aforementioned physical and chemical properties.

Evaluation of liquid crystal properties

As a result of the same observation as in Example 1, the above compound changed from an isotropic liquid into liquid crystal states of smectic A phase at 93.4° C. and chiralsmectic C phase at 66.3° C. and was finally crystallized at 15.6° C. during the cooling. On the other hand, it changed from the crystal into chiralsmectic C phase at 64.8° C. during the heating.

The spontaneous polarization was measured in the same manner as in Example 1, and consequently the compound showed a large spontaneous polarization of 266 nC/cm$^2$ at 16° C.

EXAMPLE 8

4-(2-methyloctanoyl) phenyl-3-fluoro-4-octyloxy benzoic acid ester

Synthesis of 3-fluoro-4-methoxyacetophenone

To a solution of 700 ml of dried methylene chloride and 157 g of acetyl chloride was added dropwise 267 g of anhydrous aluminum chloride over 30 minutes with stirring while holding temperature at 15°–25° C., which were further stirred at room temperature for about 2 hours. Separately, a solution of 206 g of o-fluoroanisole and 170 ml of dried methylene chloride was cooled on an ice water bath, to which was added dropwise the previously prepared solution of acetyl chloride and aluminum chloride in methylene chloride over about 2.5 hours. The resulting mixture was further stirred on the ice water bath for 1 hour and at room temperature for 1 hour. The resulting reaction mixture was poured into 1.4 l of ice water and separated into two layers. The extraction with 400 ml of methylene chloride on aqueous layer was repeated two times, and thereafter the organic layers were gathered, washed with water and dried on magnesium sulfate. After magnesium sulfate was filtered off, the filtrate was concentrated and dried to obtain a light brown crystal. This crystal was recrystallized with ethanol to obtain 242 g (yield: 88%) of a white crystal having a melting point of 89.5°–90.0° C.

Synthesis of 3-fluoro-4-hydroxyacetophenone

To 400 ml of dried toluene was added 20.4 g of 3-fluoro-4-methoxyacetophenone, which was uniformly stirred at room temperature and added with 66.1 g of anhydrous aluminum bromide over about 20 minutes. After the stirring at room temperature for 4 hours, the reaction mixture was poured into 600 ml of ice water. After the separation into two layers, the extraction with ether on aqueous layer was repeated two times, and then the organic layers were gathered, washed with water and dried on magnesium sulfate. After magnesium sulfate was filtered off, the filtrate was concentrated and dried under a reduced pressure to obtain 17.45 g of a brown crystal. This crystal was recrystallized with toluene to obtain 16.53 g (yield: 88%) of a white crystal having a melting point of 127.0°–128.2° C.

Synthesis of 3-fluoro-4-octyloxyacetophenone

After 1.70 g of sodium hydroxide was dissolved in 13 ml of water, 26 ml of ethanol and 5.10 g of 3-fluoro-4-hydroxyacetophenone were added and stirred under heating to form a homogeneous solution, and then 7.41 g of octylbromide was added thereto with stirring under heating. After the heating under reflux for 1 hour, 15 ml of acetone was added and then the heating was continued under reflux for 13 hours. After acetone and ethanol were distilled off, the reaction mixture was poured into 80 ml of water. After the extraction with ether was repeated three times, the organic layers were gathered, washed with water and dried on magnesium sulfate. After magnesium sulfate was filtered off, the filtrate was concentrated and dried under a reduced pressure to obtain 7.45 g of a slightly brown crystal. This crystal was recrystallized with a mixed solvent of methanol and water to obtain 5.07 g (yield: 58%) of a white crystal having a melting point of 39.6°–40.1° C.

Synthesis of 3-fluoro-4-octyloxy benzoic acid

After 3.10 g of sodium hydroxide was added to 26 ml of water, the resulting mixture was stirred and cooled on an ice water bath to hold temperature at 4°-8° C., to which was added 4.84 g of bromine. Then, 2.50 g of 3 fluoro-4-octyloxyacetophenone was added, and then the ice water bath was taken off to naturally return the temperature to room temperature. When the temperature reached to 20° C., 14 ml of 1,4-dioxane was added, whereby heat was generated to raise the temperature up to 45° C. After the leaving over a night, 30 ml of an aqueous solution of 2 normal hydrochloric acid was added. Then, the precipitated crystal was filtered and recrystallized with ethanol to obtain 2.09 g (yield: 83%) of a white crystal. This compound had the following physical and chemical properties, and was a liquid crystal state of nematic phase at 116° C. and finally an isotropic liquid at 121° C.

① $^1$H NMR (in $CDCl_3$, TMS standard, ppm): 7.8(2H, m), 6.98(1H, t), 4.07(2H, t), 1.82(2H, m) 1.6–1.2(10H), 0.9(3H, t)

② IR (KBr, $cm^{-1}$): 2820, 2600, 1680, 1610, 1280, 760

Synthesis of 4-(2-methyloctanoyl) phenyl-3-fluoro-4-octyloxy benzoic acid ester In 8 ml of dried methylene chloride were dissolved 0.31 g (1.3 mmol) of (+)-4-(2-methyloctanoyl) phenol obtained in the same manner as in Example 5, 0.36 g (1.3 mmol) of the above 3 fluoro-4-octyloxy benzoic acid and 18.7 mg of N,N-dimethylamino pyridine, to which was added 0.28 g (1.4 mmol) of DCC with stirring at room temperature. After the stirring for 2.5 hours, the precipitated crystal was filtered off, and then the filtrate was concentrated and dried under a reduced pressure to obtain a brown crystal. This crystal was purified through a column chromatography (silica gel-toluene) and recrystallized with ethanol to obtain 0.12 g (yield: 19%) of 4-(2-methyloctanoyl) phenyl-3-fluoro-4-octyloxy benzoic acid ester crystal having the aforementioned physical and chemical properties.

Evaluation of liquid crystal properties

As a result of the same observation as in Example 1, the above compound changed from an isotropic liquid into liquid crystal states of smectic A phase at 26.5° C. and chiralsmectic C phase at 17.4° C. and was finally crystallized at 8° C. during the cooling. On the other hand, it changed from the crystal into an isotropic liquid at 45° C. during the heating.

When the spontaneous polarization of the compound was measured in the same manner as in Example 1, it showed a large spontaneous polarization of 187 $nC/cm^2$ at 9.1° C.

EXAMPLE 9

4-(2-methyloctanoyl) phenyl-3-fluoro-4-pentyloxy benzoic acid ester

Synthesis of 3-fluoro-4-methoxy benzoic acid

A solution of 346 g of sodium hydroxide in 2.5 l of water was stirred and cooled on an ice water bath, to which was added 497 g of bromine over about 1 hour while holding liquid temperature at 6°-9° C. Then, 179 g of 3-fluoro-4-methoxyacetophenone obtained in the same manner as in Example 8 was added and thereafter the ice water bath was taken out to raise the temperature to room temperature. When the temperature exceeded 22° C., heat was generated to raise the temperature up to 45° C., and the reaction was carried out at this temperature for about 1 hour. After the leaving over a night, the reaction product was cooled on ice water, added with 50 g of sodium bisulfite to reduce excessive bromine and then added with a concentrated hydrochloric acid to adjust pH to less than 1. The precipitated crystal was filtered and recrystallized with a mixed solvent of ethanol and water to obtain 149 g (yield: 82%) of a light brown crystal.

Synthesis of 3-fluoro-4-hydroxy benzoic acid 98.8 g of 3-fluoro-4-methoxy benzoic acid was mixed with 215 ml of concentrated hydrogen bromide solution and 215 ml of acetic acid and heated under reflux for 34 hours with stirring. Thereafter, the reaction mixture was cooled with water, and the precipitated crystal was filtered to obtain a blackish brown crystal. This crystal was recrystallized with water to obtain 77.73 g (yield: 86%) of a black crystal. Moreover, the use of this crystal itself caused no problem at the subsequent step though it may be changed into white by further purification.

Synthesis of 3-fluoro-4-pentyloxy benzoic acid

A solution of 2.26 g of potassium hydroxide in 10 ml of water was added 80 ml of ethanol, 3.13 g of 3-fluoro-4-hydroxy benzoic acid and 5.94 g of 1-iodopentane, which were heated under reflux for 8 hours. Then, 20 ml of 10% potassium hydroxide was added and heated under reflux for 2 hours, and ethanol was distilled off. The reaction product was poured into 100 ml of water in a flask and added with a concentrated hydrochloric acid to adjust pH to less than 1. The precipitated crystal was filtered and recrystallized with ethanol and further with toluene two times to obtain 2.88 g (yield: 64%) of a white crystal having the following properties:

Melting point: 138.1°-138.9° C.

IR (KBr, $cm^{-1}$): 2920, 2550, 1680, 1610, 1280, 760

Synthesis of 4-(2-methyloctanoyl) phenyl-3-fluoro-4-pentyloxy benzoic acid ester The same procedure as in Example 8 was repeated, except that the above 3-fluoro-4-pentyloxy benzoic acid was used instead of 3-fluoro-4-octyloxy benzoic acid in Example 8, to obtain an objective compound having the aforementioned physical and chemical properties.

Evaluation of liquid crystal properties

As a result of the same observation as in Example 1, the above compound changed from an isotropic liquid into a crystal at 34.6° C. during the cooling, and changed from the crystal into an isotropic liquid at 58.2° C. during the heating.

EXAMPLE 10

4-(2-methyloctanoyl) phenyl-3-fluoro-4-dodecyloxy benzoic acid ester

Synthesis of 3-fluoro-4-dodecyloxy benzoic acid

The same procedure as in Example 9 was repeated, except that 1-iodododecane was used instead of 1-iodopentane in Example 9, to obtain an objective compound. This compound had the following properties:

IR (KBr, $cm^{-1}$): 2810, 2600, 1680, 1610, 1280, 760

Synthesis of 4-(2-methyloctanoyl) phenyl-3-fluoro-4-dodecyloxy benzoic acid ester The same procedure as in Example 8 was repeated, except that the above 3-fluoro-4-dodecyloxy benzoic acid was used instead of 3-fluoro-4-octyloxy benzoic acid in Example 8, to obtain an objective compound having the aforementioned physical and chemical properties.

Evaluation of liquid crystal properties

As a result of the same observation as in Example 1, the above compound changed from an isotropic liquid into a crystal at 35.4° C. during the cooling, and changed from the crystal into an isotropic liquid at 42.7° C. during the heating.

EXAMPLE 11

4-(2-methyloctanoyl) phenyl-3-fluoro-4-nonyloxy benzoic acid ester

Synthesis of 3-fluoro-4-nonyloxy benzoic acid

The same procedure as in Example 9 was repeated, except that 1-iodononane was used instead of 1-iodopentane in Example 9, to obtain an objective compound. This compound had the following properties:

IR (KBr, cm$^{-1}$): 2810, 2600, 1680, 1610, 1280, 760

Synthesis of 4-(2-methyloctanoyl) phenyl-3-fluoro-4-nonyloxy benzoic acid ester

The same procedure as in Example 8 was repeated, except that the above 3-fluoro-4-nonyloxy benzoic acid was used instead of 3-fluoro-4-octyloxy benzoic acid in Example 8, to obtain an objective compound having the aforementioned physical and chemical properties.

Evaluation of liquid crystal properties

As a result of the same observation as in Example 1, the above compound changed from an isotropic liquid into liquid crystal states of smectic A phase at 26.3° C. and chiralsmectic C phase at 20° C. and was crystallized at 19° C. during the cooling. During the heating, it changed from the crystal into an isotropic liquid at 37° C.

EXAMPLE 12

Synthesis of 4'-(2-methyloctanoyl) biphenyl-3-fluoro-4-octyloxy benzoic acid ester To 20 ml of methylene chloride were added 402 mg (1.5 mmol) of 3-fluoro 4-octyloxy benzoic acid obtained in the same manner as in Example 8 and 465 mg (1.5 mmol) of 4-hydroxy-4'-(2-methyloctanoyl) biphenyl obtained in the same manner as in Example 6 at room temperature, to which were further added 20 mg of 4-dimethylamino pyridine and 309 mg (1.5 mmol) of DCC. Thereafter, the resulting mixture was left to stand at room temperature over a night, and the precipitated solid was filtered off. The filtrate was concentrated and isolated through a column chromatography to obtain 500 mg (0.89 mmol, yield: 60%) of a white solid of 4'-(2-methyloctanoyl) biphenyl-3-fluoro-4-octyloxy benzoic acid ester having the aforementioned physical and chemical properties.

Evaluation of liquid crystal properties

As a result of the same observation as in Example 1, the above compound changed from an isotropic liquid into liquid crystal states of smectic A phase at 125.1° C. and chiralsmectic C phase at 101.4° C. and was finally crystallized at 46.3° C. during the cooling. During the heating, it changed from the crystal into chiralsmectic C phase at 72.8° C.

Further, the compound showed a large spontaneous polarization of 220 nC/cm$^2$ at 46.4° C. as measured by the same method as in Example 1.

EXAMPLE 13

3-fluoro-4-(2-methyloctanoyl) phenyl-4'-nonylbiphenyl-4-carboxylic acid ester

Synthesis of 3-fluoro-4-(2-methyloctanoyl) phenol

To 1.64 g (9.28 mmol) of (+)-2-methyl octanoic acid chloride obtained in the same manner as in Example 1 was added 1 ml of anhydrous methylene chloride, which was cooled on ice water and added with 1.41 g (10.6 mmol) of anhydrous aluminum chloride and dissolved with stirring. Separately, 1.14 g (9.04 mmol) of m-fluoroanisole and 2 ml of anhydrous methylene chloride were placed in a flask, to which was added dropwise the above solution of acid chloride and anhydrous aluminum chloride in methylene chloride over about 15 minutes while cooling on ice water. Thereafter, the resulting mixture was stirred under ice cooling for 2 hours, at room temperature for 16.5 hours and at 40° C. for 4 hours. The reaction mixture was poured into 60 ml of ice water and extracted with methylene chloride. The extract was washed with water, dried on magnesium sulfate, filtered and isolated through a column chromatography using silica gel to obtain 0.59 g (2.21 mmol, yield: 25%) of a colorless and transparent liquid of (+)-3-fluoro-4-(2-methyloctanoyl) anisole.

Then, 0.57 g (2.14 mmol) of the above (+)-3-fluoro-4-(2-methyloctanoyl) anisole and 6 ml of dried toluene were placed in a flask, to which was added 1.78 g (6.67 mmol) of anhydrous aluminum bromide while cooling on ice water. The resulting mixture was stirred under the cooling on ice water for 30 minutes and at room temperature for 6.5 hours. The reaction mixture was poured into 30 ml of ice water and extracted with toluene. The organic layer was washed with water, dried on magnesium sulfate, filtered and concentrated to obtain 0.55 g (2.18 mmol, yield: 100%) of brown oily 3-fluoro-4-(2-methyloctanoyl) phenol having the aforementioned physical and chemical properties.

Synthesis of 3-fluoro 4-(2-methyloctanoyl) phenyl-4'-nonylbiphenyl-4-carboxylic acid ester To 100 ml of dried methylene chloride were added 1.63 g of 4'-nonylbiphenyl-4-carboxylic acid obtained by hydrolysis of commercially available 4'-nonyl-4-cyanobiphenyl, 0.57 g of 3-fluoro-4-(2-methyloctanoyl) phenol and 40 mg of N,N-dimethylamino pyridine, which were stirred and slightly heated to form a homogeneous solution. The resulting solution was added with 0.84 g of DCC, stirred at 40° C. for 1 hour and at room temperature for 8 hours, and left to stand. After the precipitated white crystal was filtered off, the filtrate was concentrated and dried under a reduced pressure to obtain a yellow crystal. This crystal was purified through a column chromatography and recrystallized with ethanol to obtain 0.68 g (yield: 44%) of a white crystal having the aforementioned physical and chemical properties.

Evaluation of liquid crystal properties

As a result of the same observation as in Example 1, the above compound changed from a liquid into liquid crystal states of smectic A phase at 112.0° C. and chiralsmectic C phase at 98.5° C. and was finally crystallized at 37.3° C. during the cooling. Further, it changed from the crystal into chiralsmectic C phase at 45° C. during the heating.

Moreover, the compound showed a large spontaneous polarization of 96 nC/cm² at 38.5° C. as measured by the same method as in Example 1.

After the compound was poured into the same rubbing cell as in Example 1 and having a thickness of 5 μm, when it was observed under crossed Nicols, it was confirmed that the compound shows a uniform state at chiralsmectic C phase.

EXAMPLE 14

Synthesis of 3-fluoro-4-(2-methyloctanoyl) phenyl-4-heptyloxy benzoic acid ester To 30 ml of dried methylene chloride were added 1.36 g of commercially available 4-heptyloxy benzoic acid, 1.21 g of 3-fluoro-4-(2-methyloctanoyl) phenol obtained in the same manner as in Example 13 and 69.8 mg of N,N-dimethylamino pyridine, which were stirred to form a homogeneous solution and added with 1.18 g of DCC and reacted with stirring at room temperature for 2 hours. After the precipitated crystal was filtered off, the filtrate was washed with 2 normal hydrochloric acid, and aqueous solution of 5% sodium hydrogen carbonate and water in this order, dried on magnesium sulfate, concentrated and dried under a reduced pressure to obtain a mixture of brown crystal and oil. This mixture was purified through a column chromatography and recrystallized with ethanol to obtain 1.06 g (yield: 45%) of a white crystal of 3-fluoro-4-(2-methyloctanoyl) phenyl-4-heptyloxy benzoic acid ester having the aforementioned physical and chemical properties.

Evaluation of liquid crystal properties

As a result of the same observation as in Example 1, the compound changed from the liquid into liquid crystal states of smectic A phase at 32.0° C. and chiralsmectic C phase at 20.8° C. and was finally crystallized at 0° C. during the cooling. Further, it was smectic A phase at 30.3° C. during the heating.

Moreover, the compound showed a large spontaneous polarization of 81 nC/cm² at 15.8° C. as measured by the same method as in Example 1.

EXAMPLE 15

4-(2-methyloctanoyl) phenyl-3-fluoro-4-nonanoyloxy benzoic acid ester

Synthesis of 3-fluoro-4-nonanoyloxy benzoic acid

The same procedure as in Example 3 was repeated, except that 3-fluoro-4-hydroxy benzoic acid obtained in Example 9 was used instead of p-hydroxy benzoic acid in Example 3 and nonanoic acid chloride was used instead of decanoic acid chloride, to obtain an objective compound. This compound had the following properties:

IR (KBr, cm⁻¹): 2910, 1770, 1680, 1590, 1510, 1460, 1300, 1100, 760

Synthesis of 4-(2-methyloctanoyl) phenyl-3-fluoro-4-nonanoyloxy benzoic acid ester The same procedure as in Example 8 was repeated, except that the above 3-fluoro-4-nonanoyloxy benzoic acid was used instead of 3-fluoro-4-octyloxy benzoic acid in Example 8, to obtain an objective compound having the aforementioned physical and chemical properties.

Evaluation of liquid crystal properties

As a result of the same observation as in Example 1, the compound changed from an isotropic liquid into a crystal at 19.4° C. during the cooling, and changed from the crystal into an isotropic liquid at 39.4° C. during the heating.

EXAMPLE 16

4-(2-methylnonanoyl) phenyl-3'-fluoro-4'-octyloxybiphenyl-4-carboxylic acid ester

Synthesis of 3-fluoro-4-methoxybromobenzene

Into a flask of 5 l were charged 384 g (3.04 mol) of 2-fluoroanisole and 2.5 l of chloroform, to which was added dropwise 504 g (3.16 mol) of bromine over about 3 hours while cooling on an ice water bath at 10° C. The resulting mixture was stirred at room temperature over a night and heated under reflux for 8 hours. After the air cooling, the product was added with 1 l of water and 50 g of sodium bisulfite and sufficiently shaken to separate into two layers. The resulting organic layer was washed with an aqueous solution of 5% sodium hydrogen carbonate and further with 1 l of water and dried on magnesium sulfate. After magnesium sulfate was filtered off, the filtrate was concentrated and distilled under a reduced pressure (4 mmHg, bp: 93–°96° C.) to obtain 585 g (yield: 94%) of 3-fluoro-4-methoxybromobenzene.

Synthesis of 3-fluoro-4-methoxybiphenyl

After an inside of a flask was purged with nitrogen gas, 46 g (1.9 mol) of magnesium cut pieces was placed in the flask, while 370 g (1.80 mol) of the above 3-fluoro-4-methoxybromobenzene and 900 ml of dried tetrahydrofuran were placed in a dropping funnel. After one piece of iodine was added, the above tetrahydrofuran solution of 3-fluoro-4-methoxybromobenzene was added dropwise through the dropping funnel over about 2 hours while holding the reaction temperature at about 55° C. Then, the resulting mixture was heated under reflux for about 2 hours to synthesize 3-fluoro-4-methoxyphenyl magnesium bromide. Separately, 367 g (1.80 mol) of iodobenzene, 3.18 g (0.018 mol) of paradium chloride and 930 ml of dried tetrahydrofuran were placed in a flask of 5 l, an inside of which was purged with nitrogen gas. The above tetrahydrofuran solution of 3-fluoro-4-methoxyphenyl magnesium bromide was added dropwise over about 6 hours with stirring at room temperature. The resulting mixture was heated under reflux for 2 hours, air cooled and added with 500 ml of 10% hydrochloric acid, 500 ml of water and 1 l of hexane to separate into two layers. After the extraction with hexane on aqueous layer, the extract was gathered with the organic layer, washed with 10% saline solution and dried on magnesium sulfate. After magnesium sulfate was filtered off, the filtrate was concentrated and distilled under a reduced pressure to obtain a fraction having a boiling point of 105°–118°

C./0.4 mmHg, which was then recrystallized with ethanol to obtain 238 g (yield: 66%) of a white crystal of 3-fluoro-4-methoxy biphenyl having a melting point of 84°–86° C.

Synthesis of 4 acetyl-3'-fluoro-4'-methoxy biphenyl

Into a flask were charged 150 g (0.74 mol) of the above 3-fluoro-4-methoxy biphenyl, 1 l of carbon disulfide and 58 g (0.74 mol) of acetyl chloride, to which was added 120 g (0.90 mol) of anhydrous aluminum chloride over about 2.5 hours with stirring under ice cooling. The resulting mixture was further stirred for 2 hours and refluxed for 3 hours. After the air cooling, the reaction mixture was poured into 3 l of 1 normal hydrochloric acid. The precipitated solid was filtered and recrystallized with 2-propanol two times and with methanol to obtain 53 g (yield: 29%) of 4-acetyl-3'-fluoro-4'-methoxy biphenyl.

Synthesis of 3'-fluoro-4'-methoxybiphenyl 4-carboxylic acid

To a solution of 50 g (0.20 mol) of the above 4-acetyl 3'-fluoro-4'-methoxy biphenyl in 2 l of dioxane was added 1000 ml of an aqueous solution of sodium hypobromite (prepared from 338 g of sodium hydroxide and 486 g of bromine) over about 4 hours while cooling to not higher than 10° C., which was stirred at 25°–30° C. for about 3 hours. Thereafter, an aqueous saturated solution of sodium bisulfite was added to decompose the excessive amount of sodium hypobromite and then added with a concentrated hydrochloric acid to adjust pH to approximately 1. After the leaving over two nights, the precipitated crystal was filtered and recrystallized with ethanol and further with acetic acid to obtain 43 g (yield: 85%) of 3'-fluoro-4'-methoxybiphenyl-4-carboxylic acid.

Synthesis of 3'-fluoro-4'-hydroxybiphenyl-4-carboxylic acid

To 42 g (0.17 mol) of the above 3'-fluoro-4'-methoxybiphenyl-4-carboxylic acid were added 1.7 l of acetic acid and 300 ml of 48% hydrogen bromide solution, which was refluxed for 20 hours, poured into 3.5 l of water and air cooled. The precipitated crystal was filtered to obtain 36.4 g (yield: 92%) of 3'-fluoro-4'-hydroxybiphenyl-4-carboxylic acid.

Synthesis of 3'-fluoro-4'-octyloxybiphenyl-4-carboxylic acid

To 75 ml of an aqueous solution of 13% potassium hydroxide were added 120 ml of ethanol and 10 g (43.1 mmol) of the above 3'-fluoro-4'-hydroxybiphenyl-4-carboxylic acid, which were refluxed for 30 minutes and added with 25.0 g (129 mmol) of 1-bromooctane and then refluxed for 15 hours. After the air cooling, the precipitated crystal was filtered and recrystallized with acetic acid containing 5% hydrochloric acid and further with acetic acid to obtain 12.8 g (yield: 86.4%) of 3'-fluoro-4'-octyloxybiphenyl-4-carboxylic acid. This compound had the following properties:
IR (KBr, cm$^{-1}$): 2920, 2520, 1670, 1605, 1280, 770

Synthesis of (+)-2-methyl nonanoic acid chloride

The same procedure as in Example 1 was repeated, except that (−)-2-methyl nonanol was used instead of (−)-2-methyl-1-octanol, to obtain (+)-2-methyl nonanoic acid chloride.

Synthesis of (+)-4-(2-methylnonanoyl) phenol

The same procedure as in Example 5 was repeated, except that the above (+)-2-methyl nonanoic acid chloride was used instead of (+)-2-methyl octanoic acid chloride, to obtain (+) 4-(2-methylnonanoyl) phenol. This compound had the following properties:
IR (KBr, cm$^{-1}$): 3250, 1650, 1580
$[\alpha]^{25}_D: +9.1°$ Synthesis of 4-(2-methylnonanoyl) phenyl-3'-fluoro-4'-octyloxybiphenyl-4-carboxylic acid ester The same procedure as in Example 13 was repeated, except that the above 3'-fluoro-4'-octyloxybiphenyl-4-carboxylic acid was used instead of 4'-nonylbiphenyl-4-carboxylic acid in Example 13 and the above (+)-4-(2-methylnonanoyl) phenol was used instead of 3-fluoro-4-(2-methyloctanoyl) phenol, to obtain an objective compound having the aforementioned physical and chemical properties.

Evaluation of liquid crystal properties

As a result of the same observation as in Example 1, the above compound changed from an isotropic liquid into smectic A phase at 129.8° C. and chiralsmectic C phase at 119.0° C. and was finally crystallized at 50° C. during the cooling. During the heating, it was chiralsmectic C phase at 80° C.

Further, the compound showed a large spontaneous polarization of 296 nC/cm$^2$ at 59.0° C. as measured by the same method as in Example 1.

EXAMPLE 17

3-fluoro-4-(2-methylnonanoyl) phenyl-4'-nonylbiphenyl-4-carboxylic acid ester

Synthesis of (+)-3-fluoro-4-(2-methylnonanoyl) phenol

The same procedure as in Example 13 was repeated, except that (+)-2-methyl nonanoic acid chloride obtained in the same manner as in Example 16 was used instead of (+)-2-methyl octanoic acid chloride, to obtain an objective compound having the aforementioned physical and chemical properties.

Synthesis of 3-fluoro-4-(2-methylnonanoyl) phenyl-4'-nonylbiphenyl-4-carboxylic acid ester The same procedure as in Example 13 was repeated, except that the above (+)-3-fluoro-4-(2-methylnonanoyl) phenol was used instead of 3-fluoro-4-(2-methyloctanoyl) phenol, to obtain an objective compound having the aforementioned physical and chemical properties.

Evaluation of liquid crystal properties

As a result of the same observation as in Example 1, the above compound changed from the liquid into smectic A phase at 113.2° C. and chiralsmectic C phase at 97.8° C. and was finally crystallized at 38.4° C. during the cooling. Further, it changed from the crystal into chirasmectic C phase at 39.1° C. during the heating.

The compound showed a large spontaneous polarization of 81 nC/cm$^2$ at 42.3° C. as measured by the same method as in Example 1.

EXAMPLE 18

3-fluoro-4-(2-methylnonanoyl) phenyl-4'-hexylbiphenyl-4-carboxylic acid ester

The same procedure as in Example 13 was repeated, except that 4'-hexylbiphenyl-4-carboxylic acid obtained by hydrolysis of commercially available 4-hexyl-4'-cyanobiphenyl was used instead of 4'-nonylbiphenyl-4-carboxylic acid in Example 13 and (+)-3-fluoro-4-(2-methylnonanoyl) phenol obtained in the same manner as in Example 16 was used instead of 3-fluoro-4-(2-methyloctanoyl) phenol, to obtain an objective compound having the aforementioned physical and chemical properties.

Evaluation of liquid crystal properties

As a result of the same observation as in Example 1, the above compound changed from the liquid into liquid crystal states of smectic A phase at 116.0° C. and chiralsmectic C phase at 88° C. and was finally crystallized at 40° C. during the cooling. On the other hand, it changed from the crystal into chiralsmectic C phase at 42° C. during the heating.

Further, the compound showed a large spontaneous polarization of 78 nC/cm$^2$ at 43.0° C. as measured by the same method as in Example 1.

EXAMPLE 19

3-fluoro-4-(2-methylnonanoyl) phenyl-4'-octyloxybiphenyl-4-carboxylic acid ester The same procedure as in Example 13 was repeated, except that 4'-octyloxybiphenyl-4-carboxylic acid obtained in the same manner as in Example 1 was used instead of 4'-nonylbiphenyl-4-carboxylic acid and (+)-3-fluoro-4-(2-methylnonanoyl) phenol was used instead of 3-fluoro-4-(2-methyloctanoyl) phenol, to obtain an objective compound having the aforementioned physical and chemical properties.

Evaluation of liquid crystal properties

As a result of the same observation as in Example 1, the above compound changed from the liquid into liquid crystal states of smectic A phase at 147.8° C. and chiralsmectic C phase at 134.0° C. and was finally crystallized at 46° C. during the cooling. On the other hand, it changed from the crystal into chiralsmectic C phase at 59° C. during the heating.

Further, the compound showed a spontaneous polarization of 110 nC/cm$^2$ at 54° C. as measured by the same method as in Example 1.

EXAMPLE 20

3-fluoro-4-(2-methyloctanoyl) phenyl-3-fluoro-4-heptyloxy benzoic acid

Synthesis of 3-fluoro-4-heptyloxy benzoic acid

The same procedure as in Example 9 was repeated, except that 1-iodoheptane was used instead of 1-iodopentane in Example 9, to obtain an objective compound. This compound had the following properties:
Melting point: 123°–125° C.
IR (cm$^{-1}$) 2910, 2840, 1680, 1610, 1280, 780

Synthesis of 3-fluoro-4-(2-methyloctanoyl) phenyl-3-fluoro-4-heptyloxy benzoic acid Into a flask were charged 1.2 g (4.76 mmol) of (+)-3-fluoro 4-(2-methyloctanoyl) phenol, 1.51 g (5.94 mmol) of 3-fluoro-4-heptyloxy benzoic acid, 76.7 mg (0.63 mmol) of N,N-dimethylamino pyridine and 30 ml of dried methylene chloride, which were slightly heated with stirring to form a homogeneous solution. Then, the solution was added with 1.40 g (6.79 mmol) of dicyclohexyl carbodiimide and stirred over a night. The precipitated white crystal was filtered off, and the resulting filtrate was washed with 2 normal hydrochloric acid, an aqueous solution of 5% sodium hydrogen carbonate and water in this order and dried on magnesium sulfate. After magnesium sulfate was filtered off, the filtrate was concentrated and dried under a reduced pressure to obtain an oil. This oil was purified through a column chromatography and recrystallized with ethanol to obtain 1.02 g (2.69 mmol, yield: 44%) of a white crystal of the objective compound having the aforementioned physical and chemical properties.

EXAMPLE 21

3-fluoro-4-(2-methylnonanoyl) phenyl-3-fluoro-4-hexyloxy benzoic acid

The same procedure as in Example 20 was repeated, except that (+)-3-fluoro-4-(2-methylnonanoyl) phenol was used instead of (+)-3-fluoro-4-(2-methyloctanoyl) phenol in Example 20 and 3-fluoro-4-hexyloxy benzoic acid was used instead of 3-fluoro-4-heptyloxy benzoic acid in Example 20, to obtain an objective compound having the aforementioned physical and chemical properties.

EXAMPLE 22

3-fluoro-4-(2-methylnonanoyl) phenyl-3-fluoro-4-heptyloxy benzoic acid

The same procedure as in Example 20 was repeated, except that (+)-3-fluoro 4-(2-methylnonanoyl) phenol was used instead of (+)-3-fluoro-4-(2-methyloctanoyl) phenol in Example 20, to obtain an objective compound having the aforementioned physical and chemical properties.

EXAMPLE 23

3-fluoro-4-(2-methylnonanoyl) phenyl-3-fluoro-4-octyloxy benzoic acid

The same procedure as in Example 20 was repeated, except that (+)-3-fluoro-4-(2-methylnonanoyl) phenol was used instead of (+)-3-fluoro-4-(2-methylnonanoyl) phenol in Example 20 and 3-fluoro-4-octyloxy benzoic acid was used instead of 3-fluoro-4-heptyloxybenzoic acid in Example 20, to obtain an objective compound having the aforementioned physical and chemical properties.

EXAMPLE 24

3-fluoro-4-(2-methylnonanoyl) phenyl-3-fluoro-4-nonyloxy benzoic acid

The same procedure as in Example 20 was repeated, except that (+)-3-fluoro-4-(2-methylnonanoyl) phenol was used instead of (+)-3-fluoro-4-(2-methyloctanoyl) phenol in Example 20 and 3-fluoro-4-nonyloxy benzoic acid was instead of 3-fluoro-4-heptyloxy benzoic acid in Example 20, to obtain an objective compound having the aforementioned physical and chemical properties.

EXAMPLE 25

3-fluoro-4-(2-methylnonanoyl) phenyl-3-fluoro-4-decyloxy benzoic acid

The same procedure as in Example 20 was repeated, except that (+)-3-fluoro-4-(2-methylnonanoyl) phenol was used instead of (+)-3-fluoro-4-(2-methyloctanoyl) phenol in Example 20 and 3-fluoro-4-decyloxy benzoic acid was used instead of 3-fluoro-4-heptyloxy benzoic acid in Example 20, to obtain an objective compound having the aforementioned physical and chemical properties.

EXAMPLE 26

3-fluoro-4-(2-methylnonanoyl) phenyl-3'-fluoro-4'-octyloxybiphenyl-4-carboxylic acid Synthesis of 3-fluoro-4-(2-methylnonanoyl) phenyl-3'-fluoro-4'-octyloxybiphenyl-4-carboxylic acid The same procedure as in Example 20 was repeated, except that (+)-3-fluoro-4-(2-methylnonanoyl) phenol was used instead of (+)-3-fluoro-4-(2-methyloctanoyl) phenol in Example 20 and 3'-fluoro-4'-octyloxybiphenyl-4-carboxylic acid was used instead of 3-fluoro-4-heptyloxy benzoic acid in Example 20, to obtain an objective compound having the aforementioned physical and chemical properties.

Evaluation of liquid crystal properties

In each of the compounds in Examples 20-26, the change of texture was observed by using a polarized microscope provided with a hot stage, wherein a heating or cooling rate was 2° C./min. Furthermore, the spontaneous polarization was measured by the triangle wave method after the compound was placed in a 4 μm thick cell having ITO deposited glass plates with rubbed polyimide films. Moreover, the tilt angle was obtained from a half of moving angle of dark line when positive or negative direct current field was sufficiently applied to the cell.

The compound of Example 20 was smectic A phase at 32.2° C. and chiralsmectic C phase at 25.4° C. and was gradually crystallized from −11.1° C. during the cooling, while the crystal was fused at 39.0° C. during the heating. It showed a large spontaneous polarization of 174 nC/cm$^2$ at −4.9° C.

The compound of Example 21 was smectic A phase at 35.1° C. and chiralsmectic C phase at 18.2° C. and was crystallized at −30° C. during the cooling, while the crystal was fused at 9.3° C. to exhibit chiralsmectic C phase during the heating. It showed a large spontaneous polarization of 150 nC/cm$^2$ at −10° C. Further, the tilt angle at 5° C. was 21.7 degree.

The compound of Example 22 was smectic A phase at 33.3° C. and chiralsmectic C phase at 22.3° C. and was crystallized at −10° C. during the cooling, while the crystal was fused at 36° C. during the heating. It showed a large spontaneous polarization of 158 nC/cm$^2$ at −7.7° C. Further, the tilt angle at 12.3° C. was 23.5 degree.

The compound of Example 23 was smectic A phase at 36.7° C. and chiralsmectic C phase at 27.7° C. and was crystallized at −12° C. during the cooling, while the crystal was fused at 40° C. during the heating. It showed a large spontaneous polarization of 154 nC/cm$^2$ at −10° C. Further, the tilt angle at 20° C. was 20.0 degree.

The compound of Example 24 was smectic A phase at 37.3° C. and chiralsmectic C phase at 31.2° C. and was crystallized at −1° C. during the cooling, while the crystal was fused at 44° C. during the heating. It showed a large spontaneous polarization of 135 nC/cm$^2$ at 5° C. Further, the tilt angle at 20° C. was 23.5 degree.

The compound of Example 25 was smectic A phase at 39.3° C. and chiralsmectic C phase at 33.4° C. and was crystallized at 2° C. during the cooling, while the crystal was fused at 41° C. during the heating. It showed a large spontaneous polarization of 139 nC/cm$^2$ at 5° C. Further, the tilt angle at 20° C. was 23.2 degree.

The compound of Example 26 was smectic A phase at 133.5° C. and chiralsmectic C phase at 125.5° C. and was crystallized at 5° C. during the cooling, while the crystal was fused at 38° C. during the heating. It showed a large spontaneous polarization of 175 nC/cm$^2$ at 9.9° C. Further, the tilt angle at 40° C. was 37.5 degree.

EXAMPLE 27

Preparation of liquid crystal composition 4-(2-methyloctanoyl) phenyl 3-fluoro-4-pentyloxy benzoic acid ester obtained in Example 9 was mixed with 4-(2-methyloctanoyl) phenyl-3-fluoro-4-dodecyloxy benzoic acid ester obtained in Example 10 at various mixing ratios to prepare a phase diagram, which was shown in FIG. 1.

In FIG. 1, mark ○ shows a phase transition temperature during the cooling, and mark ● shows a temperature of fusing the crystal during the heating. The reason why the lowest temperature of chiralsmectic C phase is shown by broken lines is due to the fact that the crystallization temperature can not be specified.

4-(2-methyloctanoyl) phenyl-3-fluoro-4-pentyloxy benzoic acid ester and 4-(2-methyloctanoyl) phenyl 3-fluoro-4-dodecyloxy benzoic acid ester are substantially the same in the chemical structure but are different in the carbon number of the alkyl chain, so that they are called as a so-called homologue. As seen from FIG. 1, both the compounds do not take any liquid crystal state alone, but the mixture of these compounds takes a liquid crystal and exhibits a chiralsmectic C phase at fairly low temperature.

Moreover, the liquid crystal composition consisting of 43 mol % of 4-(2-methyloctanoyl) phenyl-3-fluoro-4-pentyloxy benzoic acid ester and 57 mol % of 4-(2-methyloctanoyl) phenyl-3-fluoro-4-docecyloxy benzoic acid ester showed a large spontaneous polarization of 98 nC/cm$^2$ at 10° C. as measured by the same method as in Example 1.

EXAMPLE 28

Preparation of liquid crystal composition

4'-(2-methyloctanoyl) biphenyl 3-chloro-4-octyloxy benzoic acid ester obtained in Example 6 was mixed with commercially available 2-[4-(6-methyloctyloxy) phenyl]-5-octylpyrimidine (hereinafter referred to as HS-98P) at va ious mixing ratios to prepare a phase diagram, which was shown in FIG. 2.

Figure 2:
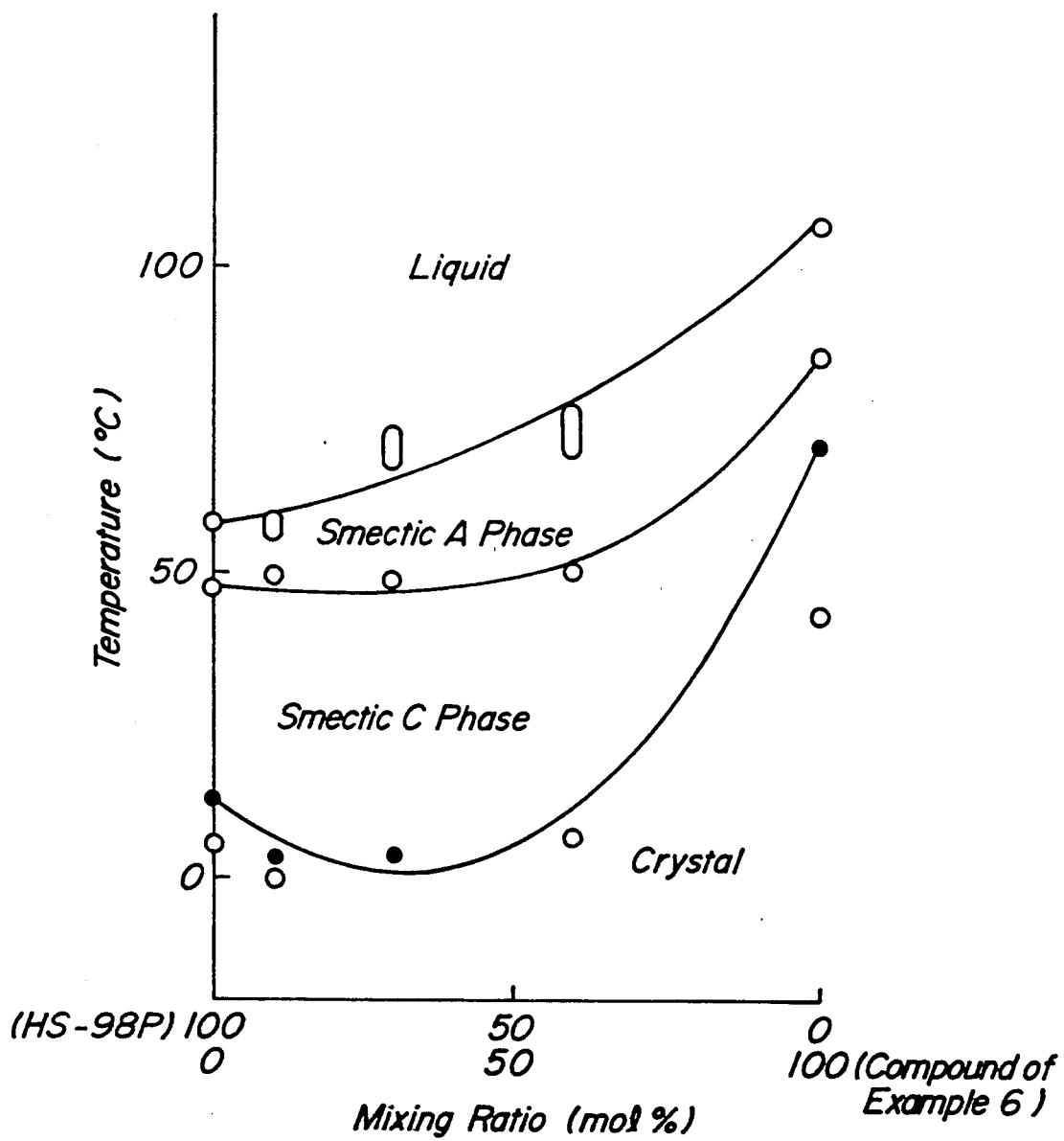
FIG. 2 is a phase diagram when 4'-(2-methyloctanoyl) biphenyl-3-chloro-4-octyloxy benzoic acid ester obtained in Example 6 and a commercially available HS-98P are mixed at various mixing ratios.

In FIG. 2, marks ○ and ● are the same as in FIG. 1. Moreover, there is a case of showing no transition point from chiralsmectic C phase to crystal, which is due to the fact that clear crystallization is not observed during the cooling.

When the spontaneous polarization was measured with respect to both the compounds at a temperature lower by 5° C. than a temperature transforming from smectic A phase to chiralsmectic C phase (T$_{AC}$), HS-98P alone showed spontaneous polarization as very low as about 0.1 nC/cm$^2$, but when 4'-(2-methyloctanoyl) biphenyl-3-chloro-4-octyloxy benzoic acid ester was added to HS-98P, the spontaneous polarization was increased. That is, the spontaneous polarization was raised to 10 nC/cm$^2$ by adding 10 mol % of the above ester, and reached to 63 nC/cm$^2$ by adding 60 mol % of the ester.

It can be seen from this result and the result of FIG. 2 that when 4'(2-methyloctanoyl) biphenyl-3-chloro-4-octyloxy benzoic acid ester is mixed at a mixing ratio of not more than 60 mol %, the range of chiralsmectic C phase is made narrower or the spontaneous polarization is increased without raising the temperature.

Figure 3:
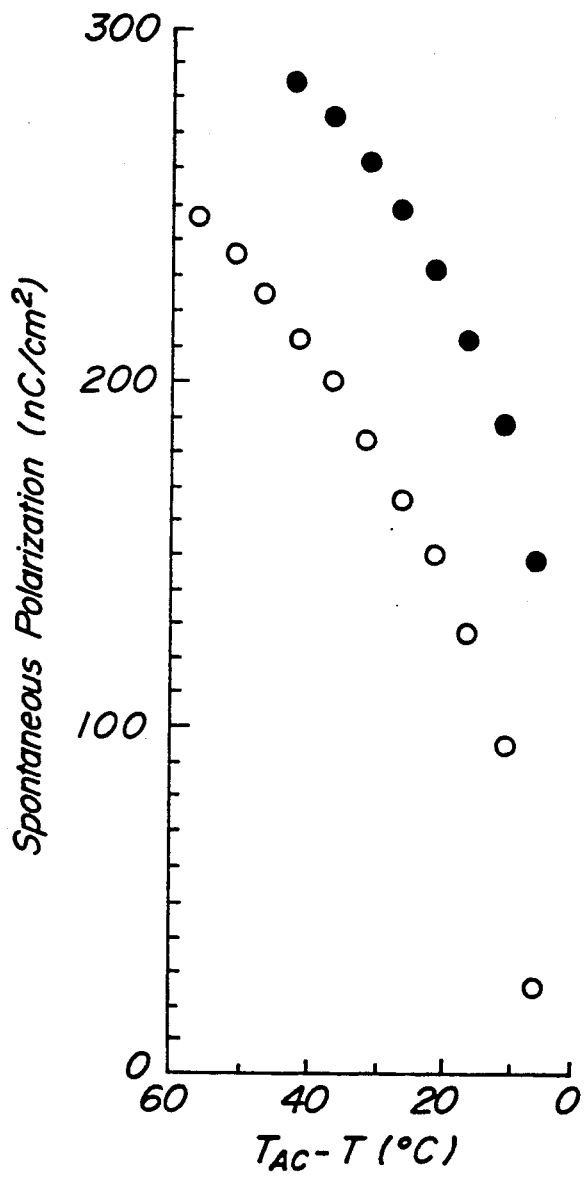
FIG. 3 is a graph showing a relation between temperature from a point ($T_{AC}$) transforming from smectic A phase to chiralsmectic C phase and spontaneous polarization in 4'-(2-methyloctanoyl) biphenyl-3 chloro-4-octyloxy benzoic acid ester obtained in Example 6 (compound of Table 1 ⑦) and a comparative compound substituting chlorine with hydrogen or 4'-(2-methyloctanoyl) biphenyl-4-octyloxy benzoic acid ester (compound of Table 1 ⑨)

Such an effect is surprising because the spontaneous polarization is hardly increased even when 4'-(2-methyloctanoyl) biphenyl-4-octyloxy benzoic acid ester obtained, for example, by substituting chlorine in 4-(2-methyloctanoyl) biphenyl-3-choloro-4-octyloxy benzoic acid ester with hydrogen is added to HS 98P in an amount of 10 mol % as shown in FIG. 3.

EXAMPLE 29

Preparation of liquid crystal composition 2-fluoro-4 (2-methyloctanoyl) phenyl-4-octyloxy benzoic acid ester obtained in Example 2 was mixed with the well-known compound of 4-octyloxyphenyl-4-octyloxy benzoic acid ester showing no ferroelectricity but chiralsmectic C phase at a mol ratio of 21:79.

As a result of the same observation as in Example 1, the above liquid crystal composition changed from an isotropic liquid into liquid crystal states of cholesteric phase at 70.5° C., smectic A phase at 63° C. and chiralsmectic C phase at 40.6° C. and was finally crystallized at 31° C. during the cooling. This chiralsmectic C phase exhibited a ferroelectricity and showed a spontaneous polarization of 9 nC/cm$^2$ at 36.5° C. as measured by the same method as in Example 1.

EXAMPLE 30

Figure 4:
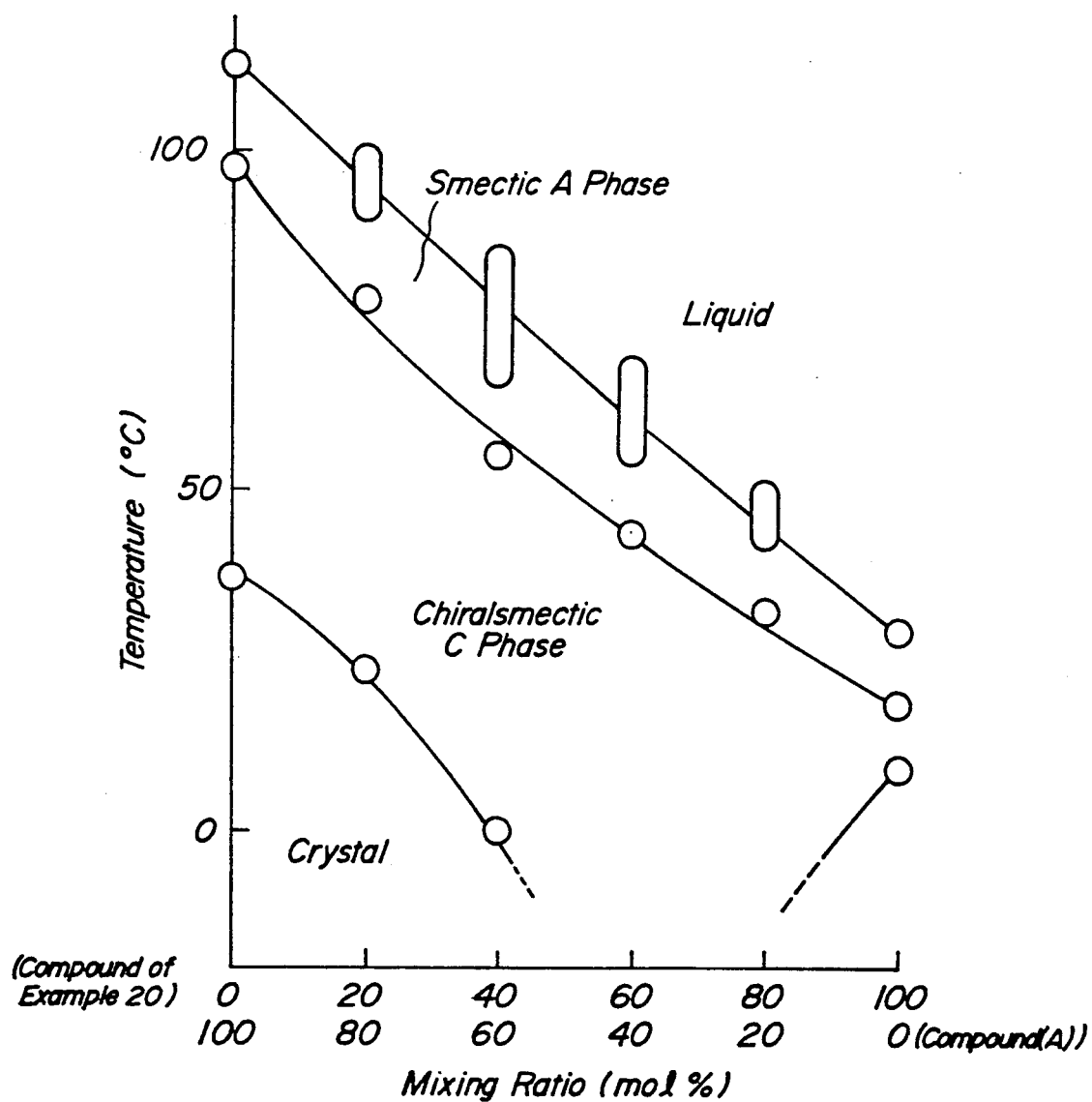
FIG. 4 is a phase diagram when 3-fluoro-4-(2-methyloctanoyl) phenyl-3-fluoro-4-heptyloxy benzoic acid ester obtained in Example 20 and 3-fluoro-4-(2-methyloctanoyl) phenyl-4'-nonylbiphenyl-4-carboxylic acid [Compound (A)] are mixed at various mixing ratios.

Preparation of liquid crystal composition 3-fluoro-4-(2-methyloctanoyl) phenyl-3-fluoro-4-heptyloxy benzoic acid obtained in Example 20 was mixed with 3-fluoro-4-(2-methyloctanoyl) phenyl-4'-nonylbiphenyl 4-carboxylic acid (A) previously found by the inventors at various mixing ratios to prepare a phase diagram, which was shown in FIG. 4.

In FIG. 4, mark ○ shows phase transformation temperature during the cooling. The reason why the lowest temperature of chiralsmectic C phase is shown by broken lines is due to the fact that the crystallization temperature can not be specified.

As seen from FIG. 4, the chiralsmectic C phase was stabilized by the mixing, so that the composition showing chiralsmectic C phase even at room temperature during the cooling could be prepared.

EXAMPLE 31

Manufacture of light switching element 4-(2-methyloctanoyl) phenyl-3-fluoro-4-octyloxy benzoic acid ester was placed in a 4 μm thick cell having ITO deposited glass plates with rubbed polyimide films and then gently cooled from a state of an isotropic liquid to orient to smectic A phase. Further, the state was changed into chiralsmectic C phase by lowering the temperature, during which when electric field was applied to the cell while observing under crossed Nicols, clear switching operation was observed.

When a rectangular wave of 32 Vpp was applied at 17° C. to the cell and a light transmitted quantity was measured by a photodiode to detect the light switching operation, the response rate was as fast as 43 μsec.

EXAMPLE 32

Manufacture of light switching element

When 3-fluoro-4-(2-methyloctanoyl) phenyl-4'-nonylbiphenyl-4-carboxylic acid ester of Example 13 was placed in a 4.8 μm thick cell having ITO deposited glass plates and pulses having a pulse width of 100 μsec and a pulse voltage of ±40 V were applied to the cell, clear switching operation was observed under crossed Nicols. Such a switching operation was switching between two uniform states, during which the change of light transmitted quantity was detected by means of a photodiode. The change of light transmitted quantity at 40° C. was shown in FIG. 5.

Figure 5:
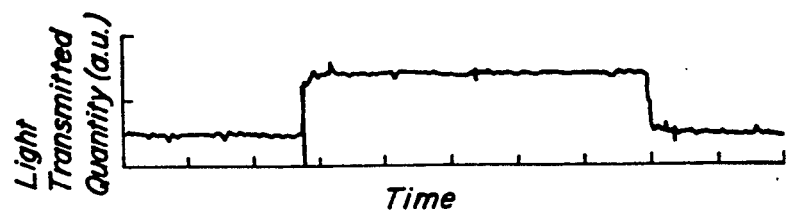
FIG. 5 is a graph showing a relation between time and light transmitted quantity in the light switching element of Example 32.

As seen from FIG. 5, it shows a very excellent bistability.

EXAMPLE 33

Manufacture of light switching element

When 3-fluoro-4-(2-methylnonanoyl) phenyl-4'-nonylbiphenyl-4-carboxylic acid ester of Example 17 was poured into the same rubbing cell having a thickness of 5.6 μm as in Example 32 and pulses having a pulse width of 2 msec and a pulse voltage of ±40 V were applied to the cell, clear switching operation was observed under crossed Nicols. Such a switching operation was switching between two uniform states, during which the change of light transmitted quantity was detected by means of a photodiode. The change of light transmitted quantity at 52° C. was shown in FIG. 6.

Figure 6:
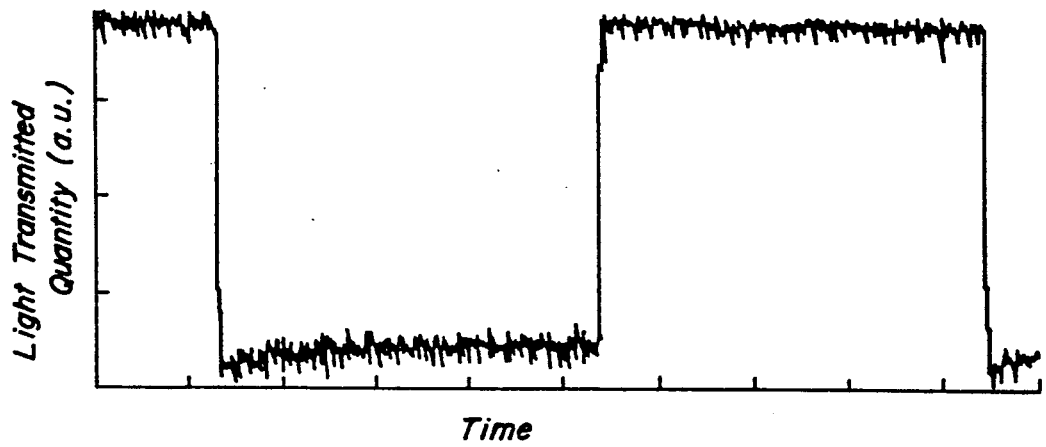
FIG. 6 is a graph showing a relation between time and light transmitted quantity in the light switching element of Example 33.

As seen from FIG. 6, it showed a very excellent bistability. Furthermore, it was excellent in the orientation and very good in the contrast because an output ratio of light state to dark state was 25:1.

EXAMPLE 34

Manufacture of light switching element

When 3-fluoro-4-(2-methylnonanoyl) phenyl-3-fluoro-4-decyloxy benzoic acid of Example 25 was observed by the same method as in Example 31, clear switching operation was observed. Further, when a rectangular wave of 10 Vpp/μm was applied at 30° C. to the cell and a light transmitted quantity was measured to detect the switching operation, the response rate was as fast as 28 μsec.

EXAMPLE 35

Manufacture of light switching element

When 3 fluoro-4-(2-methylnonanoyl) phenyl-3'-fluoro-4'-octyloxybiphenyl-4-carboxylic acid of Example 26 was observed by the same method as in Example 31, clear switching operation was observed. Further, when a rectangular wave of 10 Vpp/μm was applied at 100° C. to the cell and a light transmitted quantity was measured to detect the switching operation, the response rate was as fast as 17 μsec. Moreover, the orientation state of liquid crystal was uniform. That is, this compound was confirmed to be suitable as a light switching element.

EXAMPLE 36

Manufacture of light switching element

After 3-fluoro-4-(2-methylnonanoyl) phenyl-3-fluoro-4-heptyloxy benzoic acid of Example 23 was poured into a rubbing cell of ITO glass having a thickness of 5 μm and pulse wave having a pulse width of 2 msec and a voltage of ±40 V was applied thereto, the light transmitted quantity was measured by means of a photodiode. The change of light transmitted quantity was shown in FIG. 7.

As seen from FIG. 7, it showed a very excellent bistability.

EXAMPLE 37

Manufacture of light switching element

The light transmitted quantity in the mixture of 40 mol % of the compound of Example 20 and 60 mol % of the compound (A) as described in Example 30 was measured by the same method as in Example 36. The change of light transmitted quantity was shown in FIG. 8. As seen from FIG. 8, it showed a very excellent bistability even at room temperature.

COMPARATIVE EXAMPLE 1

Comparison with liquid crystal properties of analogous compounds having no halogen In order to more clarify the effect by the introduction of halogen, the liquid crystal properties were compared with those of the compound substituting halogen with hydrogen.

At first, the phase transformation temperatures during the cooling were shown in the following Table 1. As seen from Table 1, the shifting of chiralsmectic C phase toward low temperature side was caused by the introduction of halogen (comparison between ① and ② and between ⑤ and ⑥). This is preferable for preparing the liquid crystal composition operated at room temperature.

Further, it has been found that smectic X phase higher than chiralsmectic C phase is disappeared by the introduction of halogen (comparison between ③ and ④ and among ⑦, ⑧ and ⑨). If it is intended to widen the temperature region (particularly, lower limit) of chiralsmectic C phase by the mixing, when higher smectic X phase is existent, the temperature region of chiralsmectic C phase is not widened and the temperature region of smectic X phase is usually widened. Therefore, the disappearance of smectic X phase by the introduction of halogen is favorable if it is intended to widen the temperature region of chiralsmectic C phase by the mixing.

Moreover, the values of spontaneous polarization in the compounds ⑦ and ⑨ are shown in FIG. 3. As seen from FIG. 3, the spontaneous polarization is increased by the introduction of chlorine. The large spontaneous polarization is favorable for obtaining fast response rate.

TABLE 1

① 
(Example 8)

② 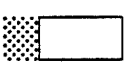
(Comparative compound)

③ 
(Example 1)

④ 
(Comparative compound)

⑤ 
(Example 13)

TABLE 1-continued

| No. | Compound | Phase transformation temperature (° C.) 0  50  100  150 |
|---|---|---|
| ⑥ |  C₉H₁₉―⟨O⟩―⟨O⟩―COO―⟨O⟩―C―C*H―C₆H₁₃<br>‖  \|<br>O  CH₃<br>(Comparative compound) |  |
| ⑦ | C₈H₁₇O―⟨O⟩―COO―⟨O⟩―C―C*H―C₆H₁₃<br>       \|                              ‖  \|<br>       Cl                             O  CH₃<br>(Example 6) |  |
| ⑧ | C₈H₁₇O―⟨O⟩―COO―⟨O⟩―⟨O⟩―C―C*H―C₆H₁₃<br>       \|                                    ‖  \|<br>       F                                    O  CH₃<br>(Example 11) |  |
| ⑨ | C₈H₁₇O―⟨O⟩―COO―⟨O⟩―⟨O⟩―C―C*H―C₆H₁₃<br>‖  \|<br>O  CH₃<br>(Comparative compound) |  |

 smectic A phase    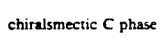 chiralsmectic C phase    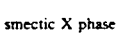 smectic X phase

COMPARATIVE EXAMPLE 2

In order to clarify the effect by introducing two halogens into the ester compound, the liquid crystal properties were compared with those of the analogous compounds. The phase transformation temperatures of various compounds during the cooling were shown in the following Table 2. In this case, the cooling rate was 2° C./min.

When comparing the compound ① with the compound ② as well as the compound ③ with the compound ④ in Table 2, it can be seen that the compounds according to the invention are stable in chiralsmectic C phase.

TABLE 2

| No. | Compound | Phase transformation temperature (° C.) 0  50  100  150 |
|---|---|---|
| ① | C₇H₁₅O―⟨O⟩―COO―⟨O⟩―C―C*HC₆H₁₃<br>       \|                \|       ‖  \|<br>       F               F       O  CH₃<br>(Example 20) | 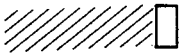 |
| ② | C₇H₁₅O―⟨O⟩―COO―⟨O⟩―C―C*HC₆H₁₃<br>       \|                       ‖  \|<br>       F                       O  CH₃<br>(Comparative compound) |  |
| ③ | C₈H₁₇O―⟨O⟩―⟨O⟩―COO―⟨O⟩―C―C*HC₆H₁₃<br>              \|                \|       ‖  \|<br>              F               F       O  CH₃<br>(Example 26) |  |

TABLE 2-continued

| No | Compound | Phase transformation temperature (°C.) 0    50    100    150 |
|----|----------|---|
| ④ | $C_9H_{19}O$—⟨◯⟩—⟨◯⟩—COO—⟨◯(F)⟩—C(=O)—C*H(CH$_3$)C$_6$H$_{13}$<br>(Comparative compound) | 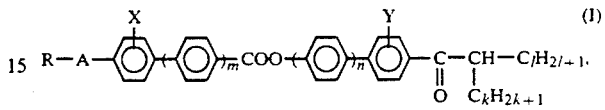 |

As seen from the above results, the compounds according to the invention can take a stable thermotropic liquid crystal state and form liquid crystals of ferroelectricity having large spontaneous polarization and a fast response rate, so that they develop a very excellent effect as a starting material for optoelectronics and their related elements.

Therefore, it can be said that the compounds according to the invention are liquid crystal materials suitable for optoelectronics and their related elements utilizing liquid crystal properties or electrochemichromism, for example, a display for liquid crystal television receiver, optical printer head, opto-Fourier transform element, light valve and the like.

What is claimed is:

1. A novel halogen-containing ester compound represented by the following general formula (I):

$$R-A-\underset{}{\underbrace{\bigcirc}}(\bigcirc)_m-COO-(\bigcirc)_n\underset{Y}{\underbrace{\bigcirc}}-\underset{O}{\overset{\|}{C}}-\underset{C_kH_{2k+1}}{\overset{|}{CH}}-C_lH_{2l+1} \quad (I)$$

wherein R is an alkyl group of 1-18 carbon atoms, A is selected from a single bond, —O—, —COO— and —CO—, both of X and Y are halogen atoms or either of X and Y is a halogen atom and the other is a hydrogen atom, each of m and n is 0 or 1 provided m+n=0 or 1, and each of k and l is an integer of 1 to 16 provided k<l.

2. The novel halogen-containing ester compound according to claim 1, wherein said compound represented by the general formula (I) is an optically active compound.

3. A liquid crystal composition containing at least one of halogen-containing ester compounds represented by the general formula (I) as claimed in claim 1.

4. A light switching element having at least one of halogen-containing ester compounds represented by the general formula (I) as claimed in claim 1 as a constituent element.

5. The halogen-containing ester of claim 1, which is 4'-(2-methyloctanoyl)biphenyl-3-chloro-4-octyloxy benzoic acid ester.

* * * * *